(12) United States Patent
Akitomo

(10) Patent No.: US 8,784,379 B2
(45) Date of Patent: Jul. 22, 2014

(54) FIXING DEVICE AND CATHETER SET

(71) Applicant: Terumo Kabushiki Kaisha, Tokyo (JP)

(72) Inventor: Dai Akitomo, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/828,540

(22) Filed: Mar. 14, 2013

(65) Prior Publication Data

US 2013/0197482 A1    Aug. 1, 2013

Related U.S. Application Data

(63) Continuation of application No. PCT/JP2011/079397, filed on Dec. 19, 2011.

(30) Foreign Application Priority Data

Feb. 25, 2011    (JP) .................................. 2011-040443

(51) Int. Cl.
*A61M 5/00*    (2006.01)

(52) U.S. Cl.
USPC ............................ 604/117; 604/523; 604/534

(58) Field of Classification Search
USPC .................. 604/117, 250, 523–527, 533–534
See application file for complete search history.

(56) References Cited

U.S. PATENT DOCUMENTS

| 5,476,493 | A | 12/1995 | Muff |
| 6,068,622 | A | 5/2000 | Sater et al. |
| 7,458,955 | B2 * | 12/2008 | Owens et al. ................. 604/117 |
| 8,435,216 | B2 * | 5/2013 | Spinoza ........................ 604/174 |

* cited by examiner

*Primary Examiner* — Theodore Stigell
(74) *Attorney, Agent, or Firm* — Novak Druce Connolly Bove + Quigg LLP

(57) ABSTRACT

A catheter set includes a catheter and a fixing device. The fixing device includes a tubular member which is formed in such a way as to increase or decrease in diameter under axial extension or compression. A first projection and a second projection are provided at both ends of the tubular member. A movable tubular body is disposed around the tubular member between the first projection and the second projection. A distal part is coupled to the tubular member by a support member. The distal part is disposed distally of the tubular member and is configured to at least contact a proximal portion of a tubular device for medical use through which the catheter runs.

20 Claims, 15 Drawing Sheets

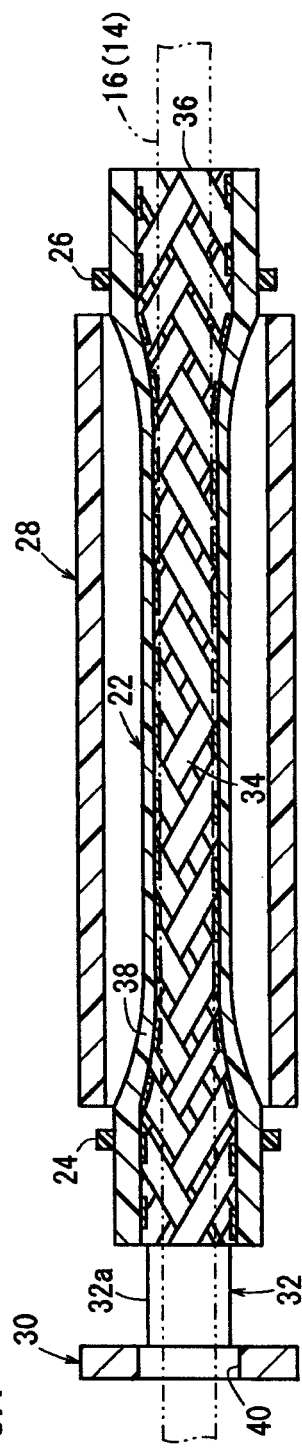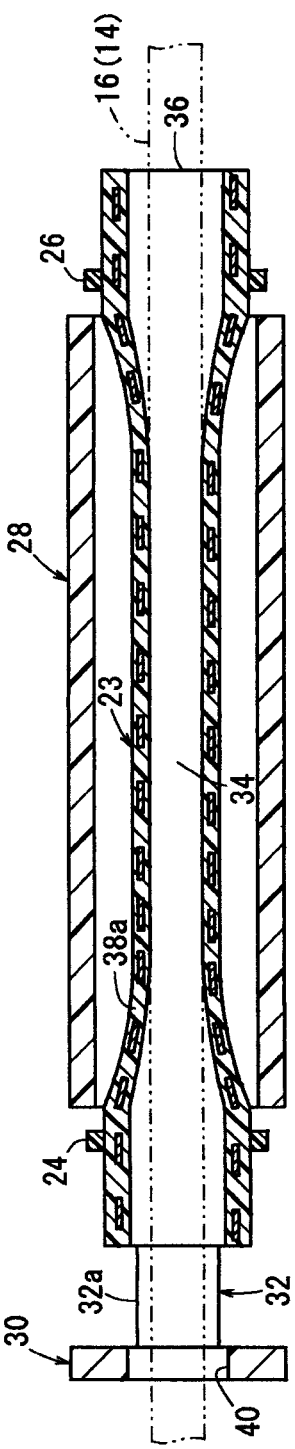

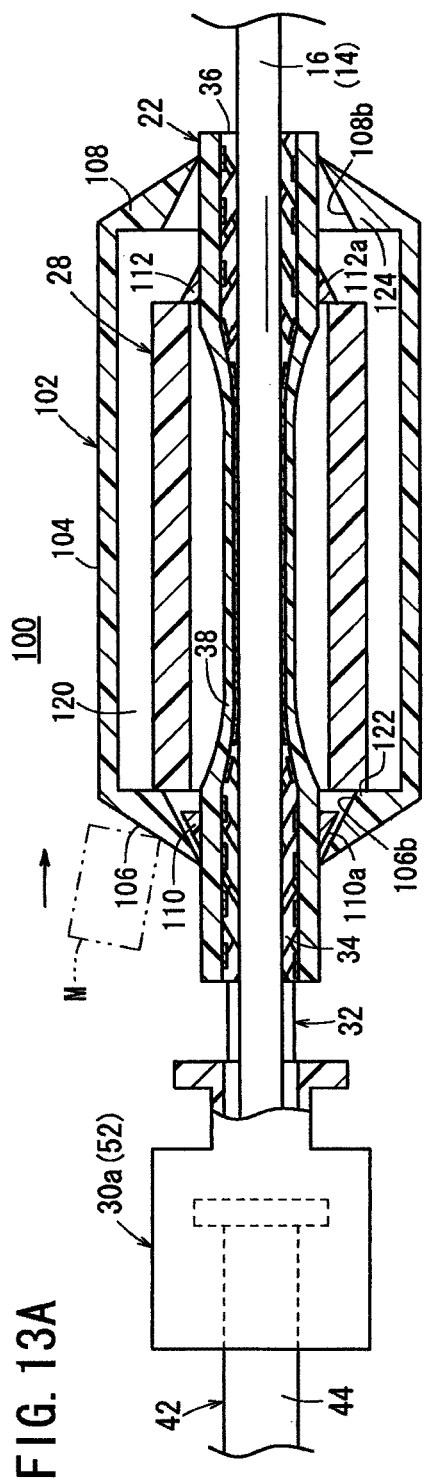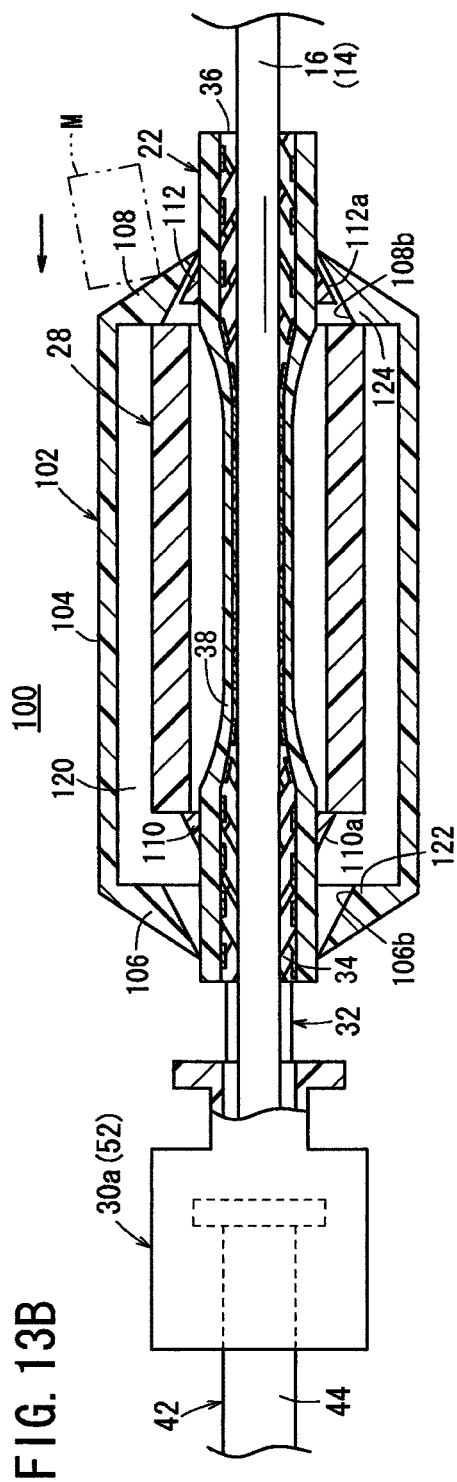

FIXING DEVICE AND CATHETER SET

CROSS-REFERENCES TO RELATED APPLICATIONS

This application is a continuation of International Application No. PCT/JP2011/079397, filed on Dec. 19, 2011, and claims priority to Japanese Application No. 2011-040443 filed on Feb. 25, 2011, the entire content of both of which is incorporated herein by reference.

TECHNICAL FIELD

The present invention relates to a fixing device which is capable of being mounted to a shaft of a catheter and capable of arbitrary change of the mounting position and fixation thereof, and to a catheter set composed of the fixing device and a catheter.

BACKGROUND

Catheters are used for insertion into a blood vessel or a body cavity to bring a catheter distal end to a target site and performing injection of a medicine for therapy or a radiopaque material for diagnosis (as a disclosure of an exemplary conventional catheter, refer to U.S. Pat. No. 6,068,622).

In the case where a catheter is percutaneously inserted into a blood vessel, for example, the catheter is inserted and passed in a sheath introducer which is preliminarily made to puncture the blood vessel through a skin. In this case, in order to maintain the distal end position of the catheter at an arbitrary position, it is desirable that the position of the catheter relative to the sheath introducer can be fixed and that the fixing position can be changed to an arbitrary position.

In the case of a catheter in which the distal end of the shaft is comparatively hard, the catheter may be used as an outer catheter, and an inner catheter having a flexible distal end may be inserted and passed in the lumen of the outer catheter. In such a situation, by advancing the catheters in the blood vessel with the distal end of the inner catheter kept protruding from the distal end of the outer catheter, the blood vessel wall can be prevented from being damaged. In this case, it is desirable that the length of projection of the distal end of the inner catheter from the distal end of the outer catheter can be kept constant, and can be changed to an arbitrary position.

SUMMARY

The present disclosure has been made in consideration of such problems as above-mentioned. Accordingly, it may be desirable to provide a fixing device capable of being mounted to a shaft of a catheter and capable of arbitrary change of the mounting position and fixation thereof, and a catheter set composed of the fixing device and a catheter.

In some aspects, the present disclosure provides a fixing device capable of being mounted to a shaft of a catheter and capable of arbitrarily changing the mounting position and fixing thereof, the fixing device characterized by including: a tubular member which has a hollow part permitting the shaft to be inserted and passed therein, and is so configured that the hollow part is enlarged by contraction in an axial direction and contracted by extension in the axial direction; a first projection and a second projection which are provided on an outer circumferential portion of the tubular member at positions spaced from each other in the axial direction of the tubular member; a movable tubular body which is disposed around the tubular member between the first projection and the second projection, and is capable of being moved in the axial direction relative to the tubular member within a range restricted by the first projection and the second projection; a distal part which is disposed on an extension of a distal direction of the tubular member directed from the second projection toward the first projection, and which is capable of at least contacting a proximal portion of a tubular device for medical use in a configuration where the fixing device is mounted to the catheter inserted and passed in a lumen of the tubular device for medical use; and a support part which links the distal part and the movable tubular body and supports the distal part.

According to the above-mentioned aspect, at the time of relatively moving the catheter in the direction for enlarging the length of insertion thereof relative to a tubular device for medical use, without touching the fixing device, the movable tubular body pushes the second projection in the rear end direction, upon contact of a distal portion of the catheter with the tubular device for medical use. In this instance, the tubular member is extended in the axial direction and the diameter in the circumferential direction of the hollow part thereof is reduced, whereby the fixing device is fixed (locked) relative to the catheter. Therefore, in regard of the direction for enlarging the length of insertion of the catheter relative to the tubular device for medical use, relative movement of the tubular device for medical use and the catheter can be inhibited. When one of the first projection and the second projection is moved toward the other, in the condition where the catheter with the fixing device mounted thereto is held, the tubular member is contracted in the axial direction and the diameter in the circumferential direction of the hollow part thereof is enlarged, resulting in that the fixing device can be moved along the catheter. Therefore, the position of the fixing device on the catheter can be changed to an arbitrary position easily and speedily.

In the above-mentioned fixing device, in some aspects, a lock part for releasable engagement with the tubular device for medical use is provided at the distal part.

In the case of such a configuration, it is ensured that when a relative movement in the direction for pulling the catheter out of the tubular device for medical use is attempted in the configuration where the lock part is in engagement with the tubular device for medical use, the first projection engages with the movable tubular body fixed to the tubular device for medical use through the lock part and the support part. This causes the tubular member to extend in the axial direction and contract in diameter, so that relative movement of the catheter and the tubular device for medical use is inhibited. In addition, when a relative movement in the direction for inserting the catheter into the tubular device for medical use is attempted in the configuration where the lock part is in engagement with the tubular device for medical use, the second projection engages with the movable tubular body fixed to the tubular device for medical use through the lock part and the support part. This causes the tubular member to extend in the axial direction and contract in diameter, so that relative movement of the catheter and the tubular member for medical use is hampered.

In the above-mentioned fixing device, in some aspects, a configuration is adopted wherein: the fixing device further includes a tubular operating part which accommodates the movable tubular body, the first projection and the second projection, is capable of being moved in the axial direction relative to the tubular member and the movable tubular body, and is operated in the axial direction; the tubular operating part has a first engaging part disposed on the distal side relative to the movable tubular body and a second engaging part disposed on the rear end side relative to the movable tubular body; the first projection has a moving range restricted between the first engaging part and a distal end of the movable tubular body; and the second projection has a moving range restricted between the second engaging part and a rear end of the movable tubular body.

In the case of such a configuration, upon an attempt to move the tubular operating part in the distal direction in the configuration where the catheter with the fixing device mounted thereto is held, the second engaging part engages with the second projection and pushes the second projection in the distal direction. This causes the tubular member to contract in the axial direction and be enlarged in diameter, so that relative movement of the catheter and the tubular device for medical use is permitted. In addition, upon an attempt to move the tubular operating part in the rear end direction in the configuration where the catheter with the fixing device mounted thereto is held, the first engaging part engages with the first projection and pushes the first projection in the rear end direction. This causes the tubular member to contract in the axial direction and be enlarged in diameter, so that relative movement of the catheter and the tubular device for medical use is permitted. Therefore, at the time of moving the position of the fixing device, it is unnecessary to selectively operate the first projection and the second projection (to change the grip from one to the other of the first and second projections), and it suffices to hold an arbitrary part of the tubular operating part and operate the tubular operating part in the axial direction. Consequently, the position of the fixing device can be changed more easily and speedily.

In the above-mentioned fixing device, in some aspects, a configuration is adopted wherein: the fixing device further includes a tubular operating part which accommodates the movable tubular body, the first projection and the second projection, is capable of being moved in the axial direction relative to the tubular member and the movable tubular body, and is operated in the axial direction; the tubular operating part has a trunk part surrounding the movable tubular body with a gap therebetween in its natural state, a first engaging part provided on a distal side of the trunk part, and a second engaging part provided on a proximal side of the trunk part, and is so configured that the first engaging part and the second engaging part are elastically decreased in diameter together with the trunk part when an inward pressing force is exerted on the trunk part; an inner circumferential portion of the first engaging part makes contact with an outer circumferential portion of the movable tubular body on the distal side relative to a part where the first projection is provided; an inner circumferential portion of the second engaging part makes contact with an outer circumferential portion of the movable tubular body on the proximal side relative to a part where the second projection is provided; the first engaging part is capable of making contact with a distal end of the movable tubular body in the state of being spaced from the first projection when the tubular operating part is in a natural state, and is capable of making contact with the first projection and operating the first projection in the axial direction when the tubular operating part is in a diametrically decreased state; and the second engaging part is capable of making contact with a proximal end of the movable tubular body in the state of being spaced from the second projection when the tubular operating part is in a natural state, and is capable of making contact with the second projection and operating the second projection in the axial direction when the tubular operating part is in the diametrically decreased state.

According to the configuration just above, the operation on the first projection or the second projection by the tubular operating part is enabled only when the tubular operating part is moved in the axial direction while being pressed inward. Therefore, even in the case where an object comes into contact with the tubular operating part in an unintentional manner, the fixation of relative positions of the catheter and the fixing device can be effectively prevented from being released.

In the above-mentioned fixing device, in some aspects, a configuration is adopted wherein: the first projection has an outer circumferential surface decreased in outside diameter as one goes away from the second projection in the axial direction; the first engaging part has an inner circumferential surface decreased in inside diameter as one goes away from the second engaging part in the axial direction; the second projection has an outer circumferential surface decreased in outside diameter as one goes away from the first projection in the axial direction; and the second engaging part has an inner circumferential surface decreased in inside diameter as one goes away from the first engaging part in the axial direction.

According to the configuration just above, even when the tubular operating part is moved in the axial direction while the tubular operating part is in the natural state, the first engaging part can be securely prevented from making contact with the first projection. In this case, besides, the second engaging part can be securely prevented from making contact with the second projection.

In the above-mentioned fixing device, in some aspects, the tubular member is a braid obtained by braiding fine lines.

In the case where the tubular member is thus composed of a braid, application of a force to the first or second projection in the axial direction results in that overlapping elements of the braided fine strands are all moved, so that the tubular member is enlarged in diameter uniformly in the circumferential direction. Specifically, linked forces are distributed uniformly in the circumferential direction, and the force is transmitted without attenuation to an end portion on the side opposite to the acting site of the force, whereby all frictional forces in the longitudinal direction are released simultaneously. Consequently, the position of the fixing device can be changed smoothly.

In the above-mentioned fixing device, in some aspects, the support part is composed of a pair of arms extending in the distal direction from the movable tubular body, and the first projection projects outward between the pair of arms.

In the case of such a configuration, since the first projection projects outward between the pair of arms, the first projection can be gripped easily. Accordingly, the position of the fixing device on the catheter can be easily changed by an operation on the first projection.

A catheter set according to the present may be characterized by including: the fixing device of any of the above-mentioned configurations; and a catheter with the fixing device mounted thereto.

Since the fixing device is thus preliminarily mounted to the catheter, an operation of mounting the fixing device in a medical care site can be omitted, which can contribute to speedy execution of a technique.

The fixing device according to the present disclosure ensures that the fixing device can be mounted to a shaft of a catheter, and the mounting position can be arbitrarily changed and fixed. The catheter set according to the present disclosure ensures that the position of the fixing device mounted to the catheter can be arbitrarily changed and the position can be fixed.

BRIEF DESCRIPTION OF DRAWINGS

FIG. 3A is a longitudinal sectional view of the fixing device according to the first embodiment, and FIG. 3B is a longitudinal sectional view of the fixing device including a tubular member according to a modification.

FIGS. 4A to 4D illustrate the operation of the fixing device according to the first embodiment, wherein FIG. 4A shows a configuration where a second projection is pushed in the distal direction relative to an inner catheter while holding the inner catheter, FIG. 4B shows a configuration where the first projection is pushed in the rear end direction relative to the inner catheter while holding the inner catheter, FIG. 4C shows a configuration where the inner catheter is moved in the direction of being pulled out of an outer catheter, and FIG. 4D shows a configuration where the inner catheter is brought closer to the outer catheter.

FIGS. 6A to 6D illustrate the operation of the fixing device according to the second embodiment, wherein FIG. 6A shows a configuration where a second projection is pushed in the distal direction relative to an inner catheter while holding the inner catheter, FIG. 6B shows a configuration where the first projection is pushed in the rear end direction relative to the inner catheter while holding the inner catheter, FIG. 6C shows a configuration where a force is exerted in the direction for spacing the inner catheter away from an outer catheter, and FIG. 6D shows a configuration where a force is exerted in the direction for bringing the inner catheter closer to the outer catheter.

FIGS. 9A to 9D illustrate the operation of the fixing device according to the third embodiment, wherein FIG. 9A shows a configuration where a force is exerted on a tubular operating part in the distal direction of the inner catheter while holding the inner catheter, FIG. 9B shows a configuration where a force is exerted on the tubular operating part in the rear end direction of the inner catheter while holding the inner catheter, FIG. 9C shows a configuration where a force is exerted in the direction for spacing the inner catheter away from the outer catheter, and FIG. 9D shows a configuration where a force is exerted in the direction for bringing the inner catheter closer to the outer catheter.

FIG. 13A shows a configuration where a force for moving the tubular operating part in the proximal direction is exerted by the contact of an object with a first engaging part of the tubular operating part of the fixing device according to the fourth embodiment, and FIG. 13B shows a configuration where a force for moving the tubular operating part in the distal direction is exerted by the contact of an object with a second engaging part of the tubular operating part of the fixing device according to the fourth embodiment.

DETAILED DESCRIPTION

Now, a fixing device and a catheter set according to the present invention will be described below by showing preferred embodiments and while referring to the attached drawings.

First Embodiment

Figure 1:
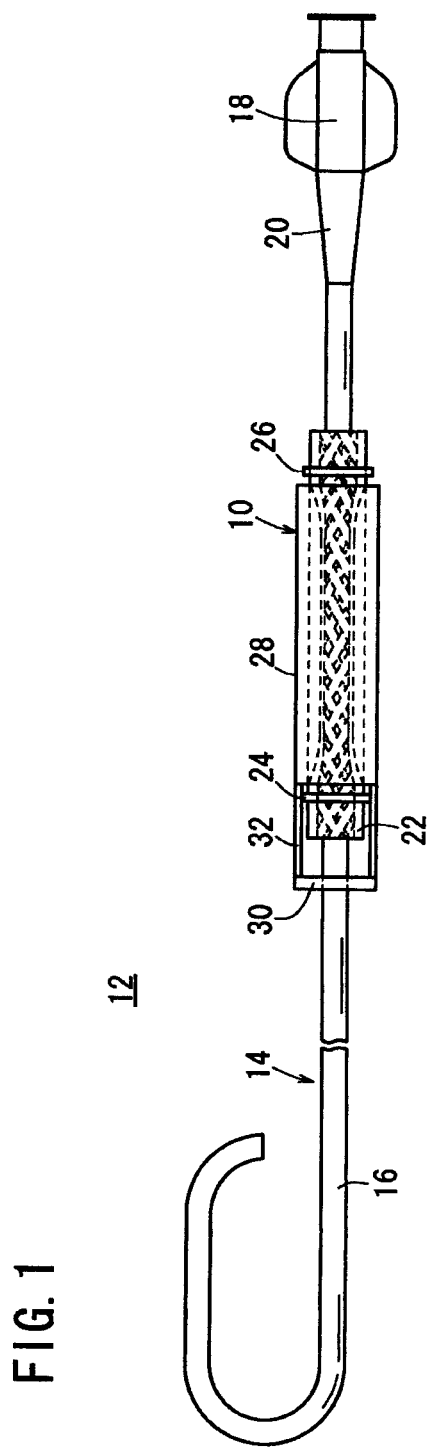
FIG. 1 is a partly omitted side view showing the general configuration of a fixing device and a catheter set provided with the fixing device, according to a first embodiment.

FIG. 1 is a partly omitted side view showing a general configuration of a fixing device 10 and a catheter set 12 provided with the fixing device 10 according to a first embodiment. The catheter set 12 is composed of a fixing device 10 and a catheter 14, the fixing device 10 being mounted on a shaft 16 of the catheter 14. Incidentally, the fixing device 10 and the catheter 14 may not necessarily be in a state where the fixing device 10 is preliminarily mounted to the catheter 14 as shown in FIG. 1; thus, the fixing device 10 may be mounted to the catheter 14 at the time of using the same.

Now, the configurations of the fixing device 10 and the catheter 14 will be described below. In the following description, in regard to the fixing device 10 and the catheter 14 and their components, the left side in FIG. 1, FIGS. 3A to 6D, FIG. 8, FIGS. 9A to 9D and FIGS. 11 to 15 will be referred to as "distal or front end or front side," and the right side as "proximal or rear end or rear side."

The catheter 14 is a medical device used for examining and/or treating a diseased part in a living body organ by being introduced into the living body organ such as a blood vessel. For example, the catheter 14 may be configured as a guiding catheter, a balloon catheter or the like for use in percutaneous transluminal coronary angioplasty (PTCA). The catheter 14 in the configuration example shown in the drawings is configured as a guiding catheter provided with a curved shape at the distal end of a shaft 16.

The catheter 14 includes a small-diameter elongated shaft 16, a hub 18 connected to the proximal end of the shaft 16, and an anti-kinking protector 20, which is provided at the distal end of the hub 18 and surrounds the outer circumference of the proximal end of the shaft 16.

The shaft 16 is formed in a hollow cylindrical shape, and is formed of a resin or the like having appropriate flexibility and appropriate strength such that the operator can smoothly insert and pass the shaft 16 into a living body organ, such as a blood vessel, while gripping and operating a proximal-side portion of the shaft 16. While a distal portion of the shaft 16 is provided with a curved shape in the example shown in the drawings, the shape may be a straight shape or a slightly curved shape according to the use of the catheter 14.

The length of the shaft 16 is set by taking into account of length from an insertion location (for example, puncture location) into the blood vessel of a human body to a target location, and operability. The shaft 16 is formed therein with a lumen extending therethrough along the longitudinal direction. In the lumen, a guide wire or a therapeutic device (for example, balloon catheter or the like) for guiding the catheter 14 to a target location is inserted and passed.

The hub 18 is a hollow member for holding a proximal portion of the shaft 16 at the distal end thereof, and is formed, for example, of a hard resin such as polycarbonate. A lumen constituting the hollow part of the hub 18 communicates with the lumen of the shaft 16. A proximal portion of the hub 18 functions as a connection port for connection with other device such as a syringe, or functions as an insertion port through which a therapeutic device may be inserted.

The anti-kinking protector 20 is for preventing bending (e.g., kinking) from occurring at a connection region of the hub 18 with the shaft 16. The anti-kinking protector 20 is, for example, formed in the shape of a tapered-off tube and formed from a resin having appropriate flexibility and rigidity.

Now, the configuration of the fixing device 10 will be described. The fixing device 10 is used by being mounted to the shaft 16 of the catheter 14, and is so configured as to enable fixation while permitting arbitrary adjustment the mounting position thereof.

Figure 2:
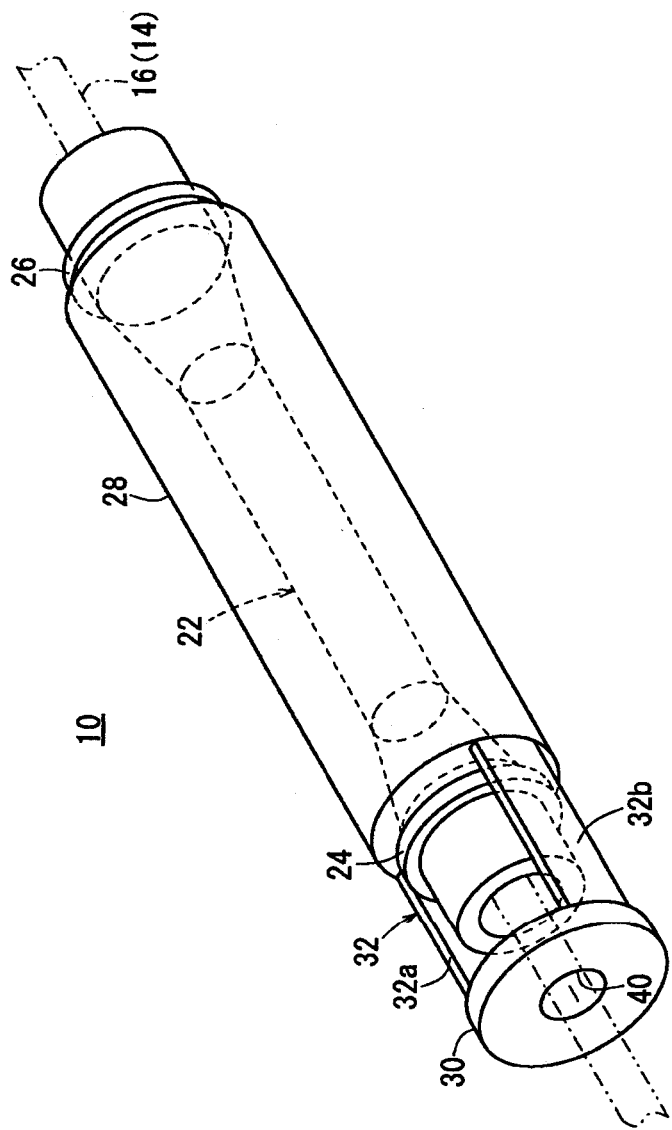
FIG. 2 is a general perspective view of the fixing device according to the first embodiment.

As shown in FIGS. 2 and 3A, the fixing device 10 includes a tubular member 22, a first projection 24 and a second projection 26 which are provided in the vicinity of both end portions of the tubular member 22, a movable tubular body 28 disposed between the first projection 24 and the second projection 26, a distal part 30 disposed on the front side of the tubular member 22, and a support part 32 which interconnects the movable tubular body 28 and the distal part 30. In various aspects, the tubular body 28 may be movable longitudinally and rotationally.

The tubular member 22 has a hollow cylindrical shape with a hollow part 34 in which the shaft 16 can be inserted and passed. The tubular member 22 is so configured that the hollow part 34 is enlarged in diameter by contraction in the axial direction (i.e., longitudinal direction) and that the hollow part 34 is reduced in diameter by elongation in the axial direction. In this embodiment, a skeleton part of the tubular member 22 is composed of a braid 36 obtained by braiding fine lines. The fine strands have rigidity, and are formed of a metal such as stainless steel or a hard resin. The braid 36 is a member in which fine strands (e.g., plate-shaped blank materials) rectangular in section are braided in a mesh form and which is tubular in general shape.

In a natural state (i.e., a state where no external force is exerted), the inside diameter of a smallest-diameter part of the tubular member 22 is set to be approximately equal to or slightly smaller than the outside diameter of the catheter 14 to be inserted and passed in the fixing device 10. In this case, the inside diameter of the tubular member 22 is preferably set so as to permit relative rotation between the fixing device 10 and the catheter 14 in the configuration where the fixing device 10 is mounted to the catheter 14, for example, via the shaft 16. This ensures that a technique of rotating the catheter 14 can be smoothly carried out, even in the configuration where the fixing device 10 is mounted to the catheter 14.

The braid 36 is so formed that its central portion in the axial direction (i.e., longitudinal direction) is smaller in diameter (i.e., smaller in the diameter of the hollow part) than its distal portion and its rear end portion. The braid 36 with such a shape can be produced by a method wherein a tubular braid (e.g., a braid as a base material) greater in diameter than the outside diameter of the shaft 16 of the catheter 14 is pulled in the longitudinal direction so as to be smaller in diameter than the outside diameter of the shaft 16. In this case, the diametrically reduced part may be either a part of or the whole of the braid 36.

In the configuration example shown in the drawings, the braid 36 has an outer circumferential portion covered substantially entirely with a resin layer 38. This resin layer 38 is formed from a material which has flexibility (e.g., elasticity) such as to permit (e.g., not to hinder) movements (e.g., extension/contraction in the axial direction, as well as enlargement and reduction in diameter) of the braid 36. For example, the same material as the resin forming the shaft 16 of the catheter 14 can be used. With such a resin layer 38 provided on the outer circumferential portion of the braid 36, it is ensured that the outer surface of the braid 36 is not exposed. Also, it is ensured that the feeling of operation at the time when the user touches and operates an end portion of the tubular member 22 can be enhanced, as compared with the case where the resin layer 38 is not provided.

When the braid 36 is repeatedly subjected to extension and contraction, the hollow part 34 would remain enlarged in diameter and would not be easily reduced in diameter (i.e., would not easily return to its natural state). With the resin layer 38 covering the fine lines, however, the fine strands can be maintained in the extended state (i.e., with the hollow part 34 kept in diametrically reduced state) in the natural configuration. In addition, with the resin layer 38 covering the fine lines, it is ensured that even when an unintentional force is exerted in the direction for enlarging the hollow part 34 in diameter, a fixed state is not easily released, since the braid 36 is insusceptible to extension and contraction.

Besides, with the resin layer 38 provided over the whole length of the braid 36, the tubular member 22 as a whole is provided with appropriate rigidity. At the time of mounting the fixing device 10 to the catheter 14, consequently, generation of deflection of the tubular member 22 can be restrained, and the operation of mounting the fixing device 10 can be carried out smoothly.

Incidentally, also on an inner circumferential portion of the braid 36, there may be provided a resin layer (e.g., inside resin layer) which is formed from the same material as the abovementioned resin layer 38. This ensures that marring of the outer surface of the shaft 16 can be prevented from occurring when the tubular member 22 makes sliding contact with the shaft 16 of the catheter 14 inserted and passed in the inside of the tubular member 22. It also ensures that the distal end of the catheter 14 can be prevented from being caught in a gap in the braid 36 when the catheter is inserted into the tubular member 22.

In place of the tubular member 22 shown in FIG. 3A, there may be used a resin layer 38a which covers the outer circumferential portion and the inner circumferential portion of the braid 36 and fills up the gaps (e.g., spaces between the fine lines) of the braid 36, as in a tubular member 23 according to a modification shown in FIG. 3B. The configuration of the tubular member 23 as just-mentioned ensures that the structure of the braid 36 is stabilized as a whole and that fixation and sliding of the fixing device 10 can be carried out smoothly. Incidentally, the tubular member 23 configured as just-mentioned can be adopted also in second and fourth embodiments and other modifications 1 and 2, which will be described later.

The first projection 24 and the second projection 26 are provided on an outer circumferential portion of the tubular member 22 at positions spaced from each other along the axial direction of the tubular member 22. In the configuration example shown in the drawings, the first projection 24 and the second projection 26 are both circular ring shaped; therefore, they project radially outward from the outer circumferential surface of the tubular member 22 and extend in the circumferential direction.

The first projection 24 is disposed in the vicinity of the distal end of the tubular member 22, and is secured to the tubular member 22 by the above-mentioned resin layer 38. The second projection 26 is disposed in the vicinity of the proximal end of the tubular member 22, and is secured to the tubular member 22 by the resin layer 38. In other words, the resin layer 38 in this embodiment also plays the role as an adhesive for fixing the first projection 24 and the second projection 26 to the tubular member 22.

The movable tubular body 28 is a member formed in a hollow cylindrical shape, and is disposed to surround the tubular member 22 between the first projection 24 and the second projection 26. The movable tubular body 28 is so configured that it can be moved in the axial direction relative to the tubular member 22 within a range limited by the first projection 24 and the second projection 26. The overall length of the movable tubular body 28 is shorter than the distance between the first projection 24 and the second projection 26.

The inside diameter of the movable tubular body 28 is greater than the outside diameter of the tubular member 22, and is smaller than the outside diameters of the first projection 24 and the second projection 26. Therefore, the movable tubular body 28 is limited in the range of axial movement relative to the tubular member 22 by the first projection 24 and the second projection 26.

The distal part 30 is a part which is disposed distally of a distal most end of the tubular member 22, and which can at least make contact with a proximal portion of a tubular device (see, e.g., FIGS. 4A-4D et seq.) for medical use in the configuration where the fixing device 10 is mounted to the catheter 14, and the catheter 14 is inserted and passed in the lumen of the tubular device for medical use.

The distance between the distal part 30 and the movable tubular body 28 (i.e., the length of the support part 32) is so set that the proximal end face of the distal part 30 and the distal end of the tubular member 22 do not make contact with each other when the movable tubular body 28 is most retracted relative to the tubular member 22. As shown in FIG. 2, the distal part 30 has an opening 40 in which the shaft 16 of the catheter 14 can be inserted and passed. In the example shown, the distal part 30 is formed in the shape of a circular ring. Incidentally, the shape of the distal part 30 is not restricted to a circular ring but may be a form of being partly divided in the circumferential direction.

The support part 32 is a part which interconnects the distal part 30 and the movable tubular body 28 and supports the distal part 30. In the configuration in the example shown, the support part 32 is composed of a pair of arms 32*a* and 32*b* which extend in the distal direction from the movable tubular body 28. The first projection 24 is projecting outward (i.e., radially outward) through a space between the pair of arms 32*a* and 32*b*. This configuration ensures that operations on the first projection 24 can be carried out assuredly by easily gripping the first projection 24.

The fixing device 10 and the catheter set 12 according to this embodiment are basically configured as above-described, and the operation and effect thereof will now be described below referring to FIGS. 4A to 4D. Referring to FIGS. 4A to 4D, a case where the tubular device for medical use in which the catheter 14 is inserted and passed is another catheter (e.g., outer catheter 42) will be described, but this example is not restrictive of the present invention. For instance, the tubular device for medical use in which the catheter 14 is inserted and passed may be a sheath introducer. This point applies also in second and third embodiments which will be described later.

In FIGS. 4A-4D, a catheter 14 with a fixing device 10 mounted onto a shaft 16 is inserted and passed in the lumen of the outer catheter 42, as an inner catheter. Incidentally, in the description made referring to FIGS. 4A to 4D, the catheter 14 will be sometimes called "the inner catheter 14."

Figure 4A:
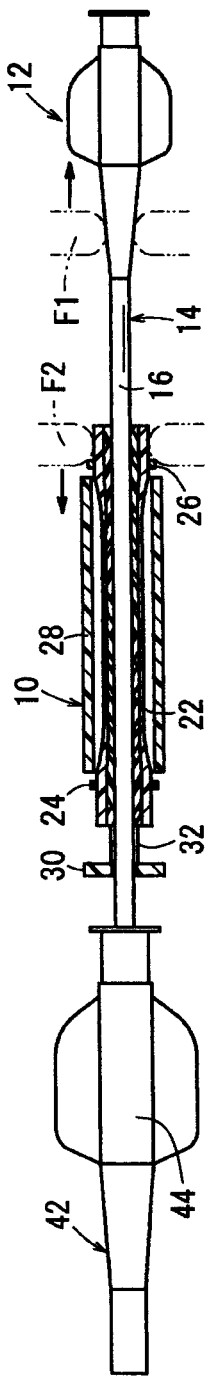

As shown in FIG. 4A, in the case where the position of the fixing device 10 is desired to be moved distally relative to the catheter 14, holding the catheter 14 by fingers F1 on one side and pushing the second projection 26 distally by fingers F2 on the other side in this configuration, as shown by the directional arrows in FIG. 4A, result in that the tubular member 22 is enlarged in diameter while contracting in the axial direction. This causes a frictional force between the tubular member 22 and the catheter 14 (the shaft 16) to be released, so that the fixing device 10 can be moved in the distal direction along the catheter 14.

Figure 4B:
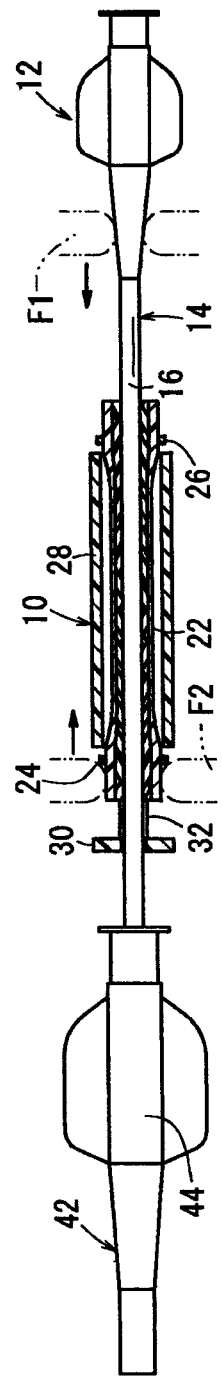

Referring to FIG. 4B, in the case where the position of the fixing device 10 is desired to be moved proximally relative to the catheter 14, holding the catheter 14 by the fingers F1 on one side and pushing the first projection 24 proximally by the fingers F2 on the other side in this configuration, as shown by the directional arrows in FIG. 4B, result in that the tubular member 22 is enlarged in diameter while contracting in the axial direction. This causes the frictional force between the tubular member 22 and the catheter 14 (the shaft 16) to be released, so that the fixing device 10 can be moved in the proximal direction along the catheter 14.

As understood from the above description made referring to FIGS. 4A and 4B, it is possible, according to the fixing device 10 in this embodiment, to change the position of the fixing device 10 on the catheter 14 to an arbitrary position easily and speedily.

Figure 4C:
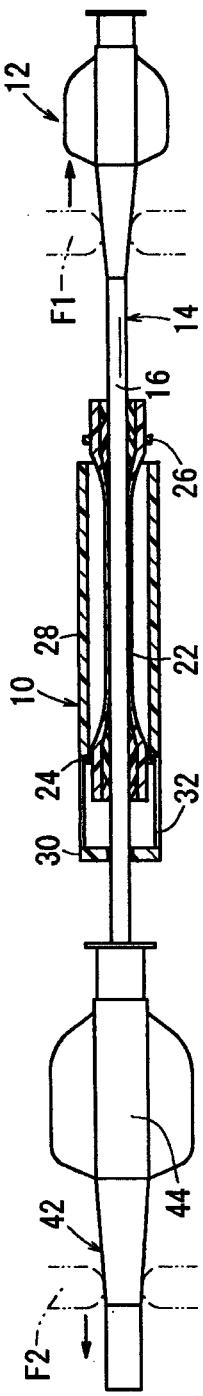

In the case of this embodiment, the fixing device 10 is not fixed in relation to the outer catheter 42. Therefore, as shown in FIG. 4C, when forces are exerted on the inner catheter 14 and the outer catheter 42 in the direction for pulling the outer catheter 42 from the inner catheter 14 in the configuration where the inner catheter 14 is held by the fingers F1 on one side and the outer catheter 42 is held by the fingers F2 on the other side, as shown by the directional arrows in FIG. 4C, the outer catheter 42 and the inner catheter 14 can be freely moved relative to each other. Thus, in the case of this embodiment, a relative movement restraining effect cannot be obtained in the direction for moving the inner catheter 14 away from the outer catheter 42.

Figure 4D:
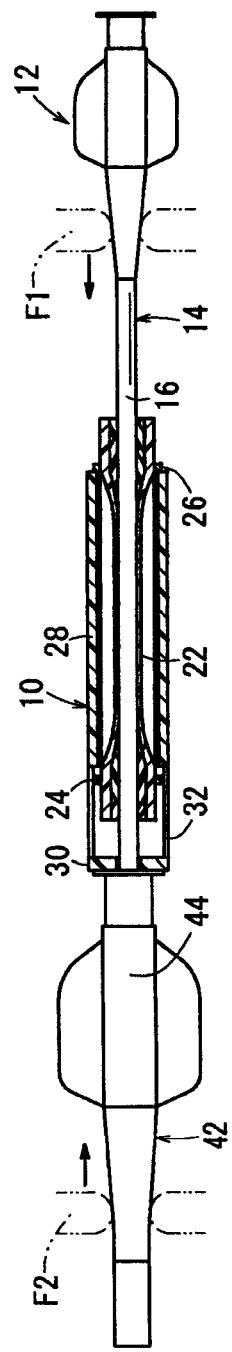

On the other hand, as shown in FIG. 4D, when forces are exerted on the inner catheter 14 and the outer catheter 42 in the direction for inserting the inner catheter 14 into the outer catheter 42 (i.e., in the direction for advancing the inner catheter 14 relative to the outer catheter 42) in the configuration where the inner catheter 14 is held by the fingers F1 on one side and the outer catheter 42 is held by the fingers F2 on the other side without holding the second projection 26, as shown by the directional arrows in FIG. 4D, the proximal end face of a hub 44 of the outer catheter 42 and the distal part 30 of the fixing device 10 soon come into contact with each other.

Then, the movable tubular body 28 pushes the second projection 26 proximally and the tubular member 22 is reduced in diameter while extending in the axial direction, whereby the fixing device 10 is fixed (i.e., locked) to the inner catheter 14. As a result, the inner catheter 14 cannot be further moved forward relative to the outer catheter 42, such that the relative positions of the outer catheter 42 and the inner catheter 14 are maintained. Therefore, the length of projection of the inner catheter 14 from the outer catheter 42 can be held constant without being enlarged.

In the case of this embodiment, the support part 32 is composed of a pair of arms 32*a* and 32*b* extending distally from the movable tubular body 28. In addition, the first projection 24 projects to the outside through a space between the pair of arms 32*a* and 32*b*. This ensures that when the first projection 24 is pushed to be operated to move proximally, the first projection 24 can be easily gripped, and the position of the fixing device 10 on the catheter 14 can be easily changed by operations on the first projection 24.

In the case of this embodiment, the tubular member 22 is composed of a braid 36 obtained by braiding fine lines. When a force is exerted on the first projection 24 or the second projection 26 in the axial direction, overlapping elements of the braided fine strands are all moved, so that the braid 36 is enlarged in diameter uniformly in the circumferential direction. Specifically, linked forces are distributed uniformly in the circumferential direction, and the force is transmitted without attenuation to an end portion on the side opposite to the acting site of the force, whereby all frictional forces in the longitudinal direction are released simultaneously. Consequently, the position of the fixing device 10 can be changed smoothly.

Where the fixing device 10 is preliminarily mounted to the catheter 14, as in the catheter set 12 shown in FIG. 1, an operation of mounting the fixing device 10 to the catheter 14 in the medical care site can be omitted, which can contribute to speedy execution of a technique.

Second Embodiment

Figure 5:
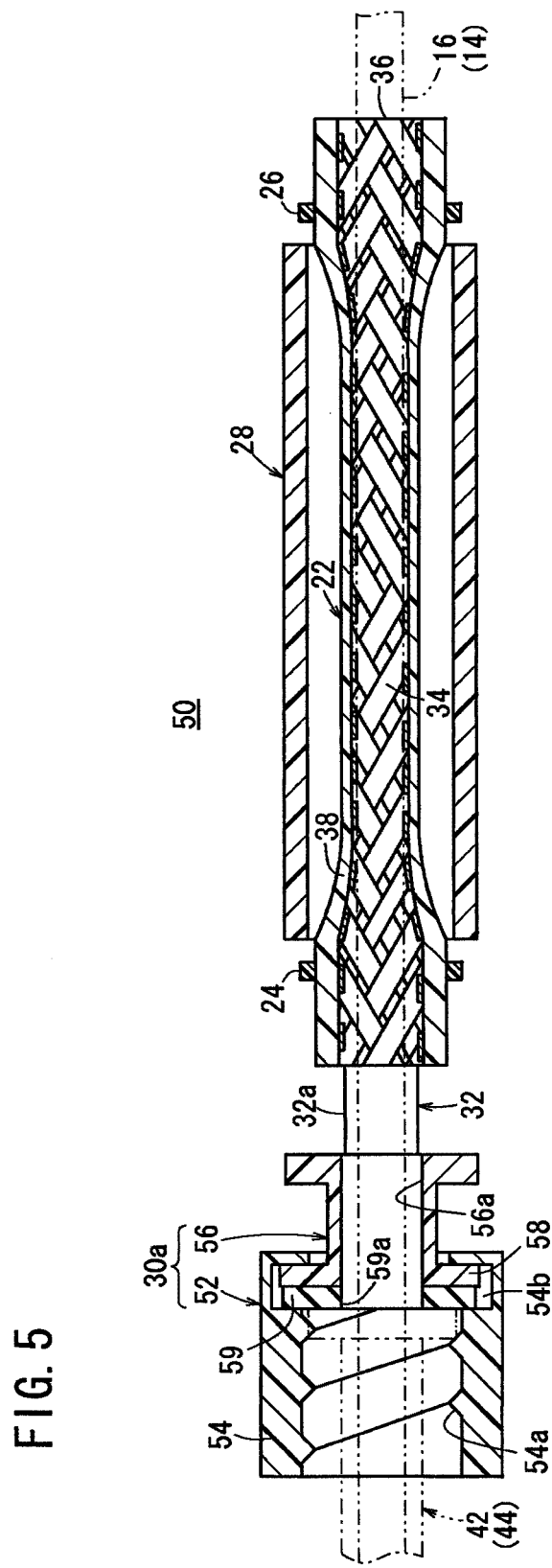
FIG. 5 is a longitudinal sectional view of a fixing device according to a second embodiment.

Now, referring to FIG. 5, a fixing device 50 according to a second embodiment will be described below. Incidentally, in the fixing device 50 according to the second embodiment, elements showing functions and effects equal or similar to those in the fixing device 10 according to the first embodiment above are denoted by the same reference signs as used above, and detailed description of such functions and effects will be omitted.

The fixing device 50 differs from the fixing device 10 according to the first embodiment in that a distal part 30a is provided with a lock part 52 for releasable engagement with a tubular device for medical use. The lock part 52 in the configuration example shown in the drawing is so configured that it can be engaged, for example, by screw fit, with a proximal portion of a medical device (for example, another catheter as an outer catheter 42, a sheath introducer, or the like) into which the catheter 14 may be inserted and passed with the fixing device 50 mounted thereto.

Specifically, the lock part 52 has a cylindrical part 54 formed with a female screw part 54a at an inner circumferential portion thereof, and a base part 56 provided at the proximal end of the cylindrical part 54. The base part 56 is formed therein with a lumen 56a in which the catheter 14 can be inserted and passed and which communicates with the inside of the cylindrical part 54. This configuration ensures that when the lock part 52 is screw engaged with a proximal portion of the tubular device for medical use, the fixing device 50 is fixed in relation to the tubular device for medical use through the lock part 52.

The base part 56 is integrally formed at the distal side thereof with a flange part 58 bulging radially outward. The flange part 58 has an outside diameter greater than the outside diameter of the base part 56, and extends in the circumferential direction over the range of 360 degrees. This flange part 58 is disposed in a space 54b formed on the proximal side of the female screw part 54a at the inner circumferential portion of the lock part 52. The flange part 58 can be rotated about the axial direction, independently from the inner circumferential portion of the lock part 52.

On the distal side of the flange part 58 in the space 54b, a valve element 59 is so disposed as to be aligned with the axial direction. The valve element 59 is, for example, a ring-shaped member formed from silicone rubber or the like. The valve element 59 is formed in its center with a hole 59a in which the catheter 14 can be inserted and passed. In addition, on the distal side of the valve element 59, a proximal end face of a tubular device for medical use (e.g., a hub 44 of an outer catheter 42) makes liquid-tight contact with the valve element 59. This configuration ensures that when the tubular device for medical use is fixed to the lock part 52 of the fixing device 50, a liquid passing through the lumen of the tubular device for medical use can be prevented from leaking out via a joint part between the tubular device for medical use and the lock part 52 of the fixing device 50. In some aspects, a branch part of a channel may be provided between the valve element 59 and the female screw part 54a.

Now, the operation and effect of the fixing device 50 according to the second embodiment will be described below. In FIGS. 6A-6D, the fixing device 50 is mounted onto the shaft 16 of the catheter 14, whereby a catheter set 51 is configured. In addition, the catheter 14 with the fixing device 50 mounted thereto is inserted and passed in the lumen of the outer catheter 42, as an inner catheter, and the lock part 52 is fixed by screw engagement (engagement) with the hub 44 of the outer catheter 42. Incidentally, in the description made referring to FIGS. 6A to 6D, the catheter 14 will sometimes be referred to as "the inner catheter 14."

Figure 6A:
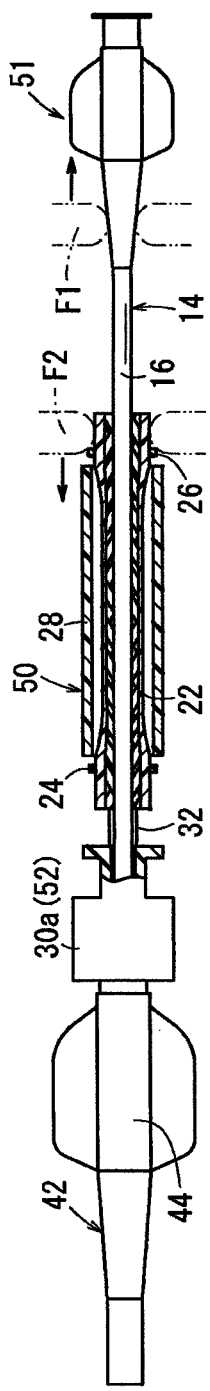

As shown in FIG. 6A, in the case where the fixing device 50 is desired to be moved distally relative to the catheter 14, holding the catheter 14 by fingers F1 on one side and pushing the second projection 26 distally by fingers F2 on the other side in this configuration, as shown by the directional arrows in FIG. 6A, result in that the tubular member 22 is enlarged in diameter while contracting in the axial direction. Consequently, a frictional force between the tubular member 22 and the catheter 14 (shaft 16) is released, so that the fixing device 50 can be moved in the distal direction along the catheter 14.

Figure 6B:
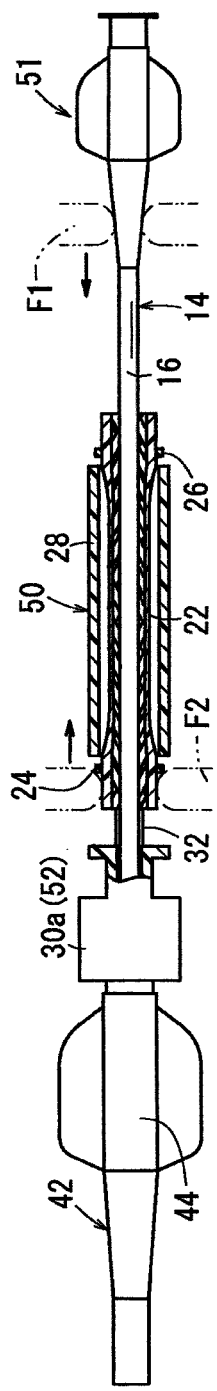

Referring to FIG. 6B, in the case where the position of the fixing device 50 is desired to be moved proximally relative to the catheter 14, holding the catheter 14 by the fingers F1 on one side and pushing the first projection 24 proximally by the fingers F2 on the other side in this configuration, as shown by the directional arrows in FIG. 6B, result in that the tubular member 22 is enlarged in diameter while contracting in the axial direction. Accordingly, a frictional force between the tubular member 22 and the catheter 14 (e.g., via shaft 16) is released, so that the fixing device 50 can be moved in the proximal direction along the catheter 14.

As understood from the above description made referring to FIGS. 6A and 6B, it is possible, according to the fixing device 50 in this embodiment, to change the position of the fixing device 50 on the catheter 14 to an arbitrary position easily and speedily, like the fixing device 10 according to the first embodiment.

Figure 6C:
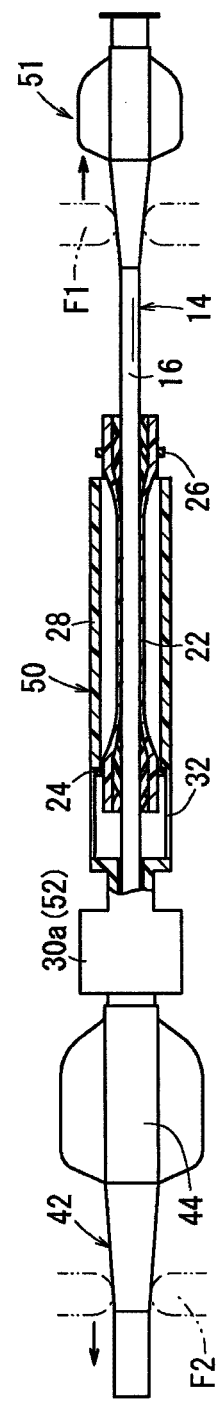

Referring now to FIG. 6C, forces are exerted on the inner catheter 14 and the outer catheter 42 in the direction for pulling the inner catheter 14 out of the outer catheter 42 in the configuration, where the inner catheter 14 is held by the fingers F1 on one side and the outer catheter 42 is held by the fingers F2 on the other side, as shown by the directional arrows in FIG. 6C. In this case, the fixing device 50 is fixed in relation to the outer catheter 42. Therefore, with the first projection 24 engaged with the movable tubular body 28, which is fixed to the outer catheter 42 through the lock part 52 and the support part 32, the tubular member 22 is reduced in diameter while extending in the axial direction, so that relative movement of the outer catheter 42 and the inner catheter 14 is inhibited.

Figure 6D:
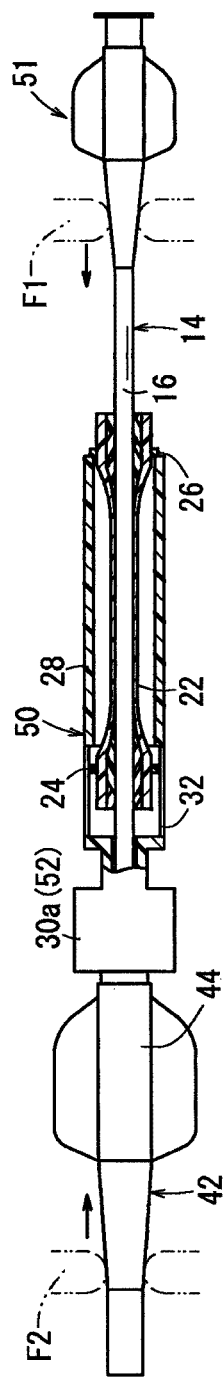

As shown in FIG. 6D, forces are exerted on the inner catheter 14 and the outer catheter 42 in the direction for inserting the inner catheter 14 into the outer catheter 42 (i.e., in the direction for advancing the inner catheter 14 relative to the outer catheter 42) in the configuration where the inner catheter 14 is held by the fingers F1 on one side and the outer catheter 42 is held by the fingers F2 on the other side, without holding the second projection 26, as shown by the directional arrows in FIG. 6D. In this case, with the second projection 26 engaged with the movable tubular body 28, which is fixed to the outer catheter 42 through the lock part 52 and the support part 32, the tubular member 22 is reduced in diameter while extending in the axial direction, so that relative movement of the outer catheter 42 and the inner catheter 14 is hampered.

As understood from the above description made referring to FIGS. 6C and 6D, it is ensured, according to the fixing device 50 in this embodiment, that an automatically locked state is realized in both of the direction for moving the catheter 14 away from the tubular device for medical use and the direction for moving the catheter 14 closer to the tubular device for medical use, whereby relative movement of the tubular device for medical use and the catheter 14 can be inhibited. Especially in the case where the tubular member for medical use is the outer catheter 42, the length of projection of the inner catheter 14 from the outer catheter 42 can be kept constant.

Incidentally, in regard of those components in the second embodiment which are provided in common in both the first and second embodiments, operations and effects equal or similar to those of the common components in the first embodiment are naturally obtained in the second embodiment.

Third Embodiment

Now, referring to FIGS. 7 and 8, a fixing device 60 according to a third embodiment will be described below. Incidentally, in the fixing device 60 according to the third embodiment, elements showing functions and effects equal or similar to those in the fixing devices 10 and 50 according to the first and second embodiments are denoted by the same reference signs as used above, and detailed description of such elements will be omitted.

The fixing device 60 differs from the fixing device 50 according to the second embodiment in that it has a tubular operating part 62 in which a movable tubular body 28, a first projection 24 and a second projection 26 are accommodated. The tubular operating part 62 is a part which is slidable in the axial direction (i.e., longitudinal direction) relative to a tubular member 22 and the movable tubular body 28, and which is operated to move in the axial direction by the user (i.e., operator).

The tubular operating part 62 in the configuration example shown is formed in the shape of a hollow cylinder having openings (for example, a distal opening 64 and a proximal opening 66) at both ends in the axial direction thereof. From the distal opening 64 of the tubular operating part 62, a distal portion of the tubular member 22 and a pair of arms 32a and 32b protrude in the distal direction. From the proximal opening 66 of the tubular member 22, a proximal portion of the tubular member 22 protrudes in the proximal direction.

The tubular operating part 62 is a part to be pinched with fingers and operated by the user. Preferably, the tubular operating part 62 has an appropriate length and an appropriate outside diameter for easy pinching and, further, is provided at its outer circumferential surface with a projection(s) or a groove(s) for an anti-slipping purpose. The material forming the tubular operating part 62 is not particularly restricted. For example, a hard resin such as polycarbonate or a metal such as stainless steel is used as the material.

Figure 8:
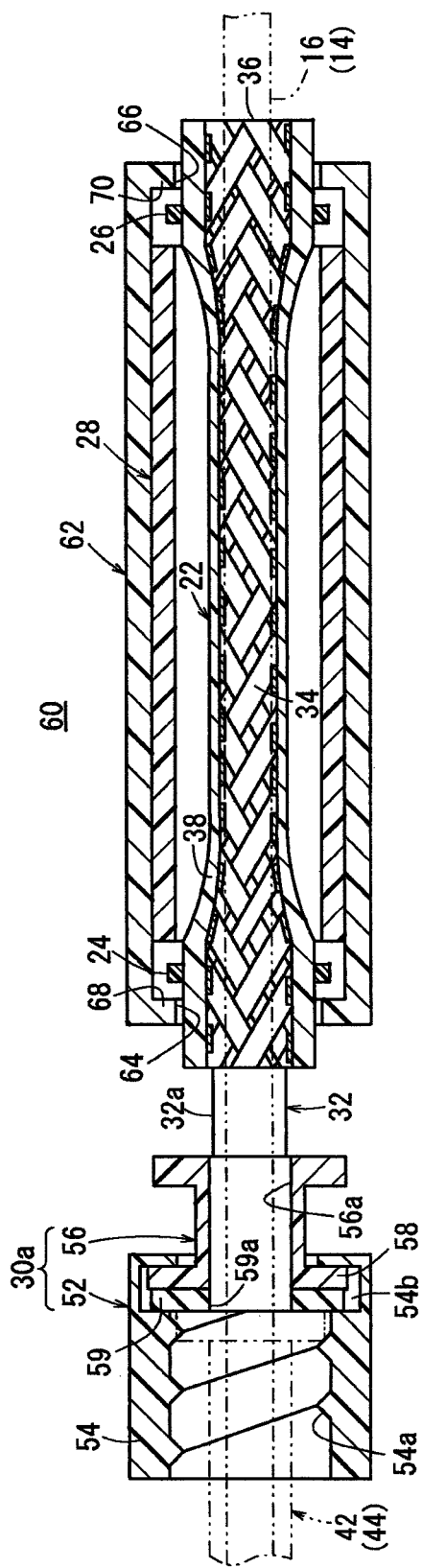
FIG. 8 is a longitudinal sectional view of the fixing device according to the third embodiment.

As shown in FIG. 8, the tubular operating part 62 has a first engaging part 68 disposed on the distal side relative to the movable tubular body 28, and a second engaging part 70 disposed on the proximal side relative to the movable tubular body 28. In the configuration example shown in the drawing, the first engaging part 68 is a distal wall projecting inward from the distal end of a trunk part of the tubular operating part 62, and the distal opening 64 is defined by the inner circumferential surface of the first engaging part 68. In the configuration example shown, the second engaging part 70 is a proximal wall projecting inward from the proximal end of the trunk part of the tubular operating part 62, and the proximal opening 66 is defined by the inner circumferential surface of the second engaging part 70.

The inside diameter of the first engaging part 68 is greater than the outside diameter of the tubular member 22 and is smaller than the outside diameter of the first projection 24. Therefore, the first projection 24 has a moving range restricted between the first engaging part 68 and the distal end of the movable tubular body 28. The inside diameter of the second engaging part 70 is greater than the outside diameter of the tubular member 22 and is smaller than the outside diameter of the second projection 26. Therefore, the second projection 26 has a moving range restricted between the second engaging part 70 and the rear end of the movable tubular body 28.

Now, referring to FIGS. 9A to 9D, the operation and effect of the fixing device 60 according to the third embodiment will be described below. As shown in FIGS. 9A-9D, the fixing device 60 is mounted onto the shaft 16 of the catheter 14, whereby a catheter set 61 is configured. In addition, the catheter 14 with the fixing device 60 mounted thereto is inserted and passed in the lumen of an outer catheter 42, as an inner catheter, and a lock part 52 is fixed by engagement, such as, for example, screw engagement, with a hub 44 of the outer catheter 42. Incidentally, in the description to be made referring to FIGS. 9A to 9D, the catheter 14 will sometimes be referred to as "the inner catheter 14."

Figure 9A:
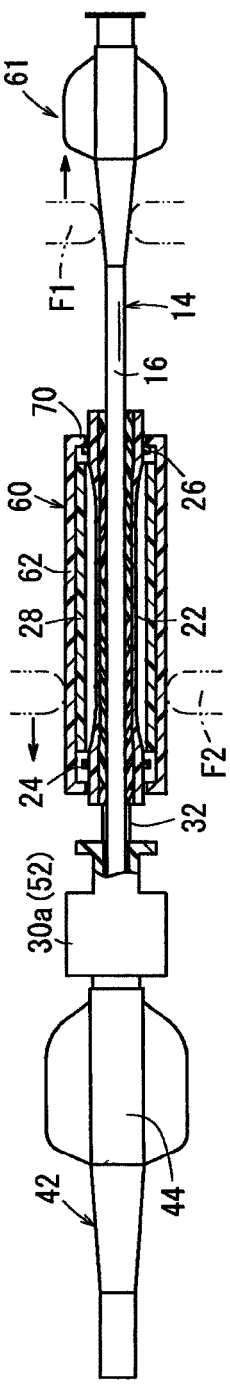

As shown in FIG. 9A, in the case where the fixing device 60 is desired to be moved distally relative to the catheter 14, the catheter 14 is held by fingers F1 on one side, and, in this configuration, an arbitrary portion of the tubular operating part 62 is gripped with fingers F2 on the other side and the tubular operating part 62 is pushed in the distal direction, as shown by the directional arrows in FIG. 9A. Then, the second engaging part 70 of the tubular operating part 62 engages with the second projection 26 and pushes it distally, whereby the tubular member 22 is enlarged in diameter while contracting in the axial direction. Consequently, the fixing device 60 can be moved in the distal direction along the catheter 14.

Figure 9B:
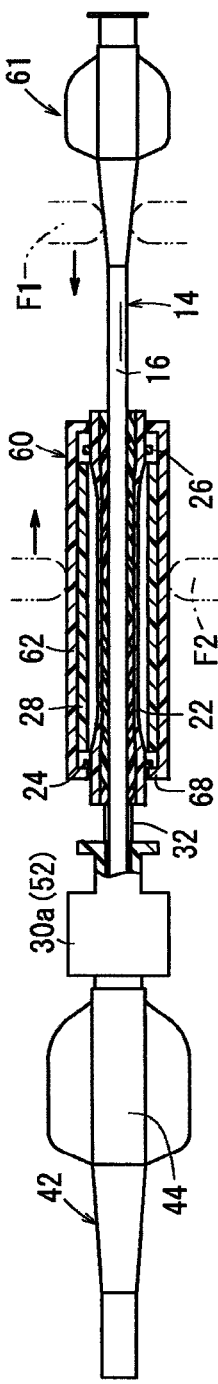

Referring to FIG. 9B, in the case where the position of the fixing device 60 is desired to be moved in the proximal direction with respect to the catheter 14, the catheter 14 is held by fingers F1 on one side, and, in this configuration, an arbitrary portion of the tubular operating part 62 is gripped with fingers F2 on the other side and the tubular operating part 62 is pushed in the proximal direction, as shown by the directional arrows in FIG. 9B. Then, the first engaging part 68 engages with the first projection 24 and pushes it proximally, whereby the tubular member 22 is enlarged in diameter while contracting in the axial direction. As a result, the fixing device 60 can be moved in the proximal direction along the catheter 14.

As understood from the above description made referring to FIGS. 9A and 9B, it is ensured, according to the fixing device 60 in this embodiment, that at the time of moving the position of the fixing device 60 relative to the catheter 14 it is unnecessary to selectively operate the first projection 24 and the second projection 26 (i.e., to change the grip from one to the other of the first and second projections 24, 26). It suffices to hold an arbitrary portion of the tubular operating part 62 and operate it in the axial direction. Therefore, the position of the fixing device 60 can be changed more easily and speedily.

Figure 9C:
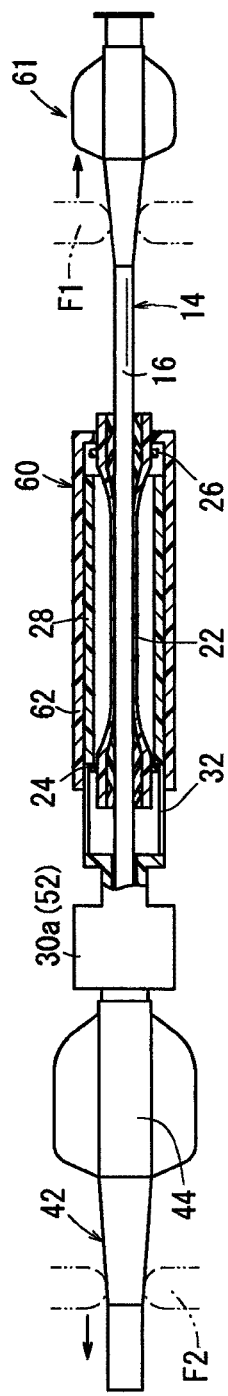

Referring now to FIG. 9C, in the configuration where the inner catheter 14 is held by fingers F1 on one side and the outer catheter 42 is held by fingers F2 on the other side, forces are exerted on the inner catheter 14 and the outer catheter 42 in the direction for pulling the inner catheter 14 from the outer catheter 42, as shown by the directional arrows in FIG. 9C. In this case, since the fixing device 60 is fixed relative to the outer catheter 42, due to the engagement of the first projection 24 with the movable tubular body 28, which is fixed to the outer catheter 42 through the lock part 52 and the support part 32, the tubular member 22 is reduced in diameter while extending in the axial direction. Consequently, relative movement of the outer catheter 42 and the inner catheter 14 is inhibited.

Figure 9D:
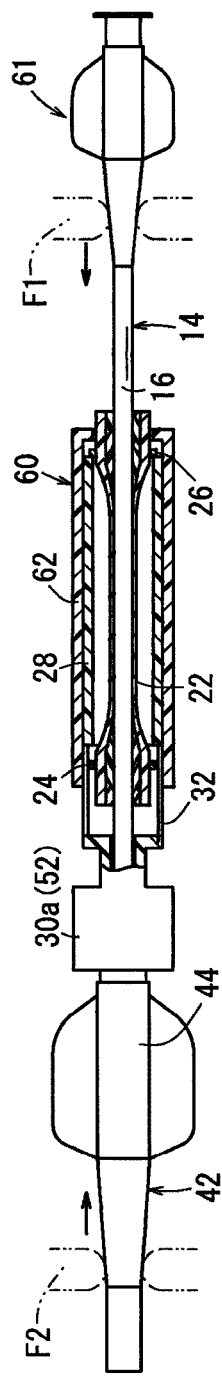

As shown in FIG. 9D, in the configuration where the inner catheter 14 is held by fingers F1 on one side and the outer catheter 42 is held by fingers F2 on the other side without holding the second projection 26, as shown by the directional arrows in FIG. 9D, forces are exerted on the inner catheter 14 and the outer catheter 42 in the direction for inserting the inner catheter 14 into the outer catheter 42 (i.e., in the direction for advancing the inner catheter 14 relative to the outer catheter 42). In this case, due to the engagement of the second projection 26 with the movable tubular body 28, which is fixed to the outer catheter 42 through the lock part 52 and the support part 32, the tubular member 22 is reduced in diameter while extending in the axial direction. Therefore, relative movement of the outer catheter 42 and the inner catheter 14 is hampered.

As understood from the above description made referring to FIGS. 9C and 9D, it is ensured, according to the fixing device 60 in this embodiment, that an automatically locked state is realized both in the direction for moving the catheter 14 away from the tubular device for medical use and in the direction for moving the catheter 14 closer to the tubular device for medical use, so that relative movement of the tubular device for medical use and the catheter 14 is inhibited, like in the case of the fixing device 50 according to the second embodiment. In this instance, the tubular operating part 62 cannot prevent axial movement of the movable tubular body 28 within the restricted moving range, and is moved independently from the movable tubular body 28.

Fourth Embodiment

Now, referring to FIGS. 10 to 13B, a fixing device 100 according to a fourth embodiment will be described below. Incidentally, in the fixing device 100 according to the fourth embodiment, elements having functions and effects equal or similar to those in the fixing devices 10, 50, and 60 according to the first to third embodiments are denoted by the same reference signs as used above, and detailed descriptions of such elements will be omitted. The fixing device 100 according to this embodiment differs from the fixing device 60 according to the third embodiment in configuration of a second projection 112 and a tubular operating part 102.

Figure 10:
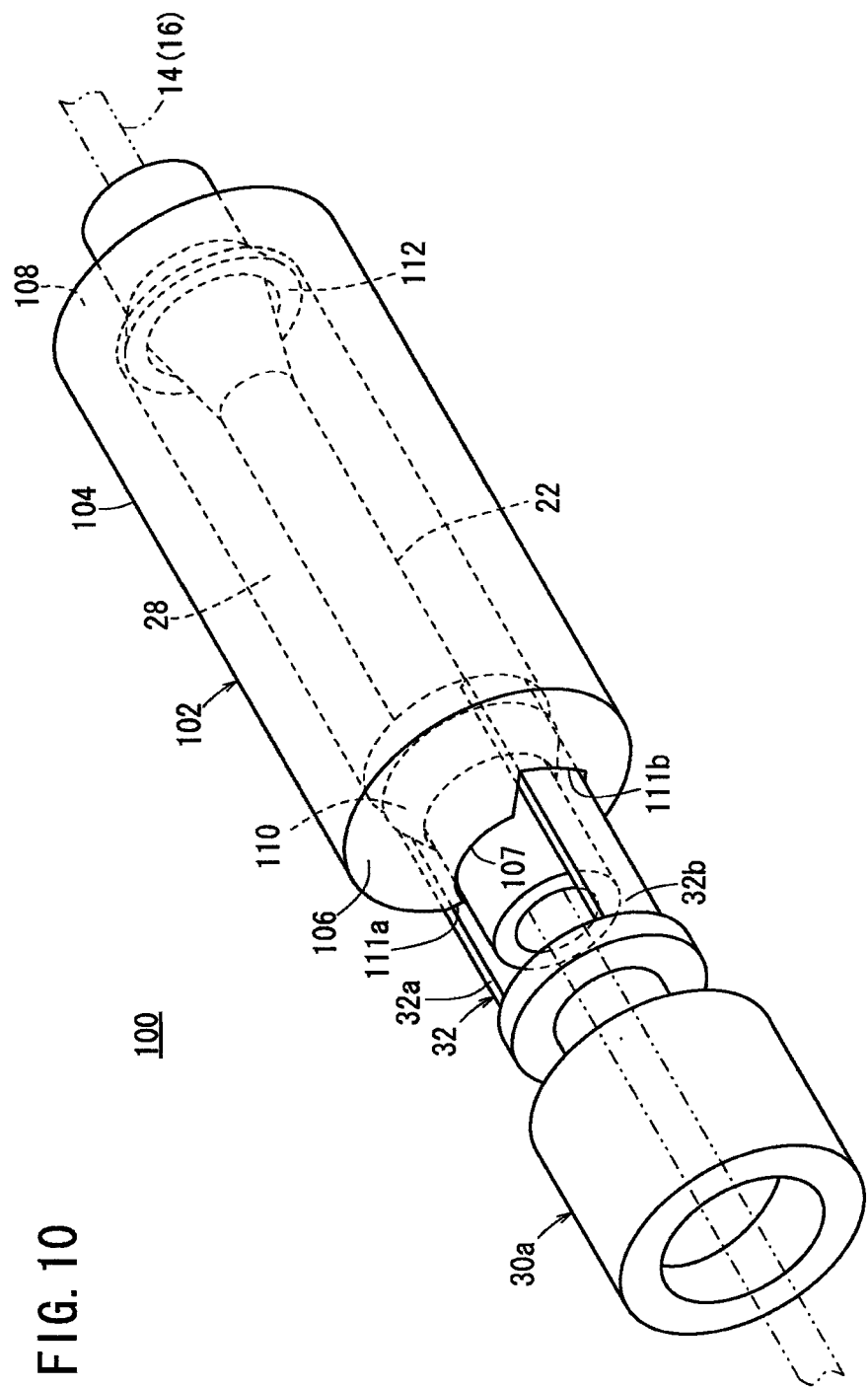
FIG. 10 is a general perspective view of a fixing device according to a fourth embodiment.
Figure 11:
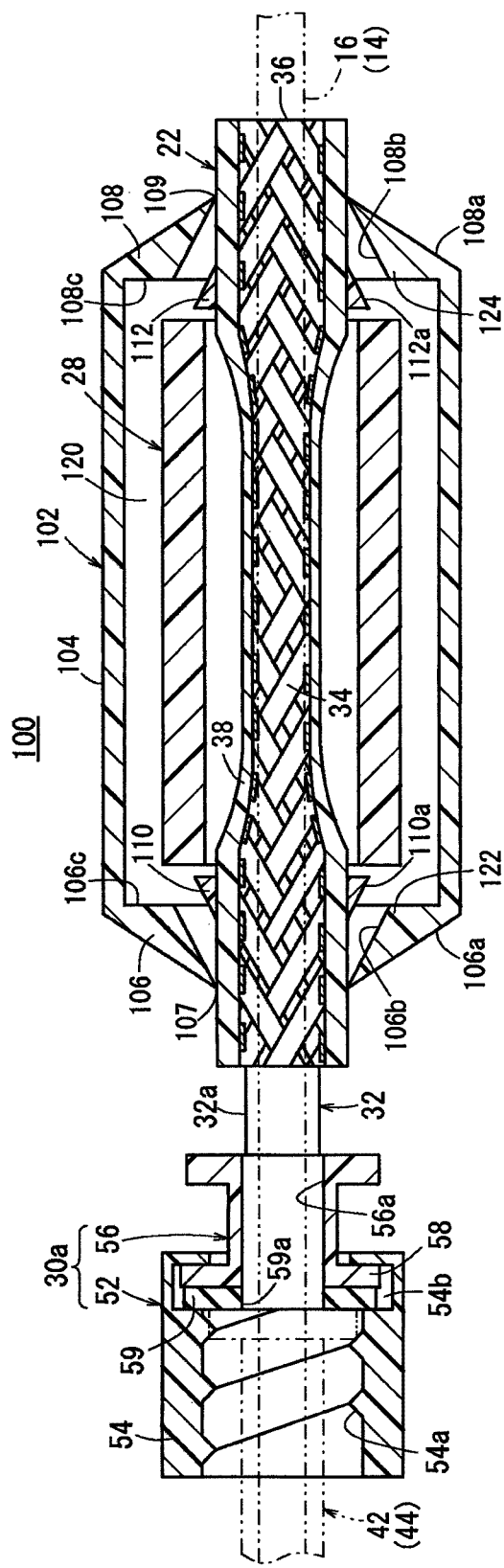
FIG. 11 is a longitudinal sectional view of the fixing device according to the fourth embodiment.

As shown in FIGS. 10 and 11, a first projection 110 and the second projection 112 are provided on an outer circumferential portion of the tubular member 22 at positions spaced from each other in the axial direction of the tubular member 22. The first projection 110 and the second projection 112 are each formed in the shape of a circular ring; therefore, they project radially outward from the outer circumferential surface of the tubular member 22 and extend in the circumferential direction.

The first projection 110 is disposed at a position deviated a little distally from the distal end position of the tubular member 22 in the proximal direction of the fixing device 100, and is secured to the tubular member 22 by a resin layer 38. The first projection 110 in this embodiment has an outer circumferential surface 110a decreased in diameter as one goes away from the second projection 112 in the axial direction. The second projection 112 is disposed at a position deviated a little proximally from the proximal position of the tubular member 22 in the distal direction of the fixing device 100, and is secured to the tubular member 22 by the resin layer 38. Unlike the above-mentioned second projection 26, the second projection 112 in this embodiment has an outer circumferential surface 112a decreased in outside diameter as one goes away from the first projection 110 in the axial direction. The spacing between the first projection 110 and the second projection 112 is greater than the overall length of the movable tubular body 28, and the outside diameter(s) of the first projection 110 and the second projection 112 is greater than the inside diameter of the movable tubular body 28. Therefore, the movable tubular body 28 is so disposed as to be movable in the axial direction within a restricted range between the first projection 110 and the second projection 112.

Figure 7:
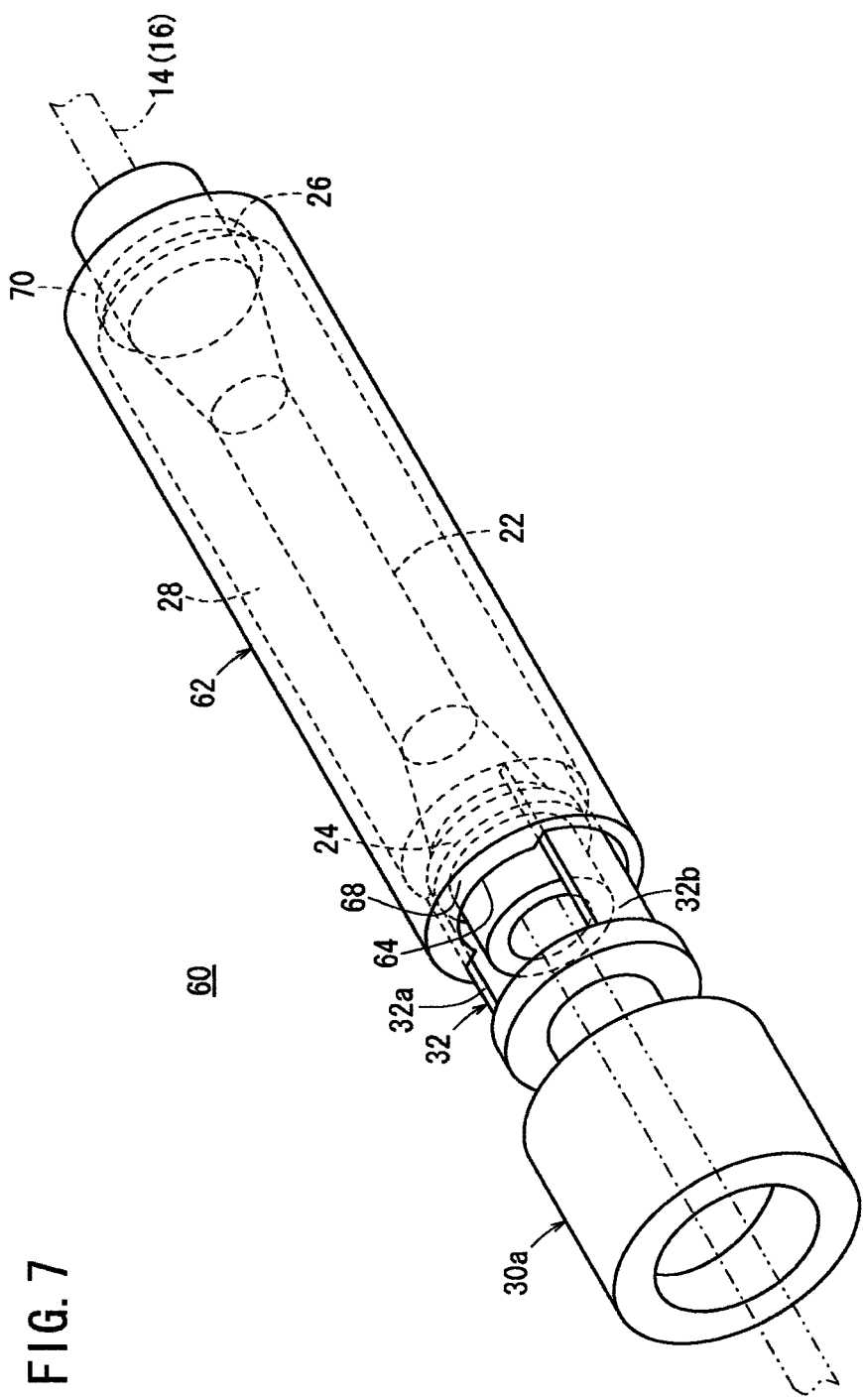
FIG. 7 is a general perspective view of a fixing device according to a third embodiment.

The tubular operating part 102 is the same as the tubular operating part 62 shown in FIG. 7 and the like, in that it is a part which accommodates the first projection 110, the second projection 112 and the movable tubular body 28, which is movable in the axial direction (i.e., longitudinal direction) relative to the tubular member 22 and the movable body 28, and which is operated to move in the axial direction by the user (i.e., operator). However, the tubular operating part 102 differs from the tubular operating part 62 in the following points.

The tubular operating part 102 includes a trunk part 104 surrounding the movable tubular body 28 with a gap therebetween in a natural state, a first engaging part 106 provided on the distal side of the trunk part 104, and a second engaging part 108 provided on the proximal side of the trunk part 104. When the trunk part 104 receives inward pressures from both sides thereof orthogonal to the axial direction, the first engaging part 106 and the second engaging part 108 are reduced in diameter through elastic deformation together with the trunk part 104.

The overall length of the trunk part 104 is greater than the overall length of the movable tubular body 28, and the inside diameter of the trunk part 104 is greater than the outside diameter of the movable tubular body. Therefore, at least in a natural state of the tubular operating part 102, an annular gap 120 extending in the axial direction is formed between the trunk part 104 and the movable tubular body 28, over the whole length of the movable tubular body 28. Incidentally, the term "natural state" used in regard to the tubular operating part 102 means a state of the tubular operating part 102 not being reduced in diameter through elastic deformation (i.e., non reduced-in-diameter state).

In this embodiment, the tubular operating part 102 is formed in the shape of a hollow cylinder which includes an opening at both ends in the axial direction thereof. The first engaging part 106 is a distal wall projecting inward and distally from the distal end of the trunk part 104 of the tubular operating part 102. The second engaging part 108 is a proximal wall which projects inward and proximally from the proximal end of the trunk part 104 of the tubular operating part 102.

A distal portion of the tubular member 22 protrudes distally from an opening 107 of the first engaging part 106 that is provided on the distal side. A proximal portion of the tubular member 22 protrudes proximally from an opening 109 of the second engaging part 108 that is provided on the proximal side. The first engaging part 106 is provided, at its locations (e.g., two locations) corresponding to a pair of arms 32a and 32b of a support part 32, with notches 111a and 111b (see FIG. 10) which communicate with the opening 107. The arms 32a and 32b are protruding distally through the notches 111a and 111b.

The first engaging part 106 is configured as follows. When the tubular operating part 102 is in the natural state, the first engaging part 106 can make contact with the distal end of the movable tubular body 28, which may be spaced from the first projection 110. When the tubular operating part 102 is in a diametrically reduced state, the first engaging part 106 can make contact with the first projection 110 and operate the first projection 110 in the axial direction. In addition, the second engaging part 108 is configured as follows. When the tubular operating part 102 is in the natural state, the second engaging part 108 can make contact with the proximal end of the movable tubular body 28, which may be spaced from the second projection 112. When the tubular operating part 102 is in a diametrically reduced state, the tubular operating part 102 can make contact with the second projection 112 and operate the second projection 112 in the axial direction. In this embodiment, the first engaging part 106 and the second engaging part 108 are specifically configured as follows.

The inside diameter of the first engaging part 106 and the inside diameter of the second engaging part 108 are each approximately equal to or a little greater than the outside diameter of the tubular member 22. An inner edge of the first engaging part 106 is in contact with the outer circumferential surface of the tubular member 22 on the distal side relative to the first projection 110. An inner edge of the second engaging part 108 is in contact with the outer circumferential surface of the tubular member 22 on the proximal side relative to the second projection 112. As a result, the tubular operating part 102 is supported on the outer circumferential surface of the tubular member 22 at the inner edge of the first engaging part 106 and the inner edge of the second engaging part 108, in the configuration where an annular gap 120 is formed between the inner circumferential surface of the trunk part 104 and the outer circumferential surface of the movable tubular body 28. In addition, the inside diameter of the first engaging part 106 and the inside diameter of the second engaging part 108 may each be slightly smaller than the outside diameter of the tubular member 22. In this case, also, the tubular operating part 102 makes contact with the outer circumferential surface of the tubular member 22 at the inner edge of the first engaging part 106 and the inner edge of the second engaging part 108, and is supported by the outer circumferential surface of the tubular member 22.

In this embodiment, the first engaging part 106 has an outer circumferential surface 106a and an inner circumferential surface 106b decreased in diameter along the direction away from the trunk part 104. The angle of inclination of the outer circumferential surface 106a relative to the axis is greater than the angle of inclination of the inner circumferential surface 106b relative to the axis. In addition, the inner surface of the tubular operating part 102 is provided with a first angular part 122 at a radial-directionally middle position of the first engaging part 106 (i.e., a site between the inner end of the first engaging part 106 and the trunk part 104). The first angular part 122 is composed of an inner edge portion of a surface 106c forming a part between the tapered inner circumferential surface 106b of the first engaging part 106 and the inner circumferential surface of the trunk part 104. The inside diameter at the proximal end of the first angular part 122 is smaller than the outside diameter of the movable tubular body 28.

In this embodiment, the second engaging part 108 has an outer circumferential surface 108a and an inner circumferential surface 108b decreased in diameter in the direction away from the trunk 104. The angle of inclination of the outer circumferential surface 108a relative to the axis is greater than the angle of inclination of the inner circumferential surface 108b relative to the axis. In addition, the inner surface of the tubular operating part 102 is provided with a second angular part 124 at a radial-directionally middle position of the second engaging part 108 (i.e., a site between the inner end of the second engaging part 108 and the trunk part 104).

The second angular part 124 is composed of an inner edge portion of a surface 108c forming a part between the tapered inner circumferential surface 108b of the second engaging part 108 and the inner circumferential surface of the trunk part 104. The inside diameter at the distal end of the second angular part 124 is smaller than the outside diameter of the movable tubular body 28. The spacing between the first angular part 122 and the second angular part 124 is greater than the whole length of the movable tubular body 28. This ensures that in the natural state, the tubular operating part 102 is freely displaceable in the axial direction relative to the movable tubular body 28 within a range restricted between the first angular part 122 and the second angular part 124.

The material forming the tubular operating part 102 is not specifically restricted, insofar as the tubular operating part 102 is elastically deformed and the first engaging part 106 and the second engaging part 108 are reduced in diameter together with the trunk part 104 when the trunk part 104 is pinched with fingers and a force is applied thereto by the operator. Examples of the material include comparatively flexible synthetic resins. Specific examples of the comparatively flexible synthetic resins include various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin or styrene, and mixtures of them.

Figure 12A:
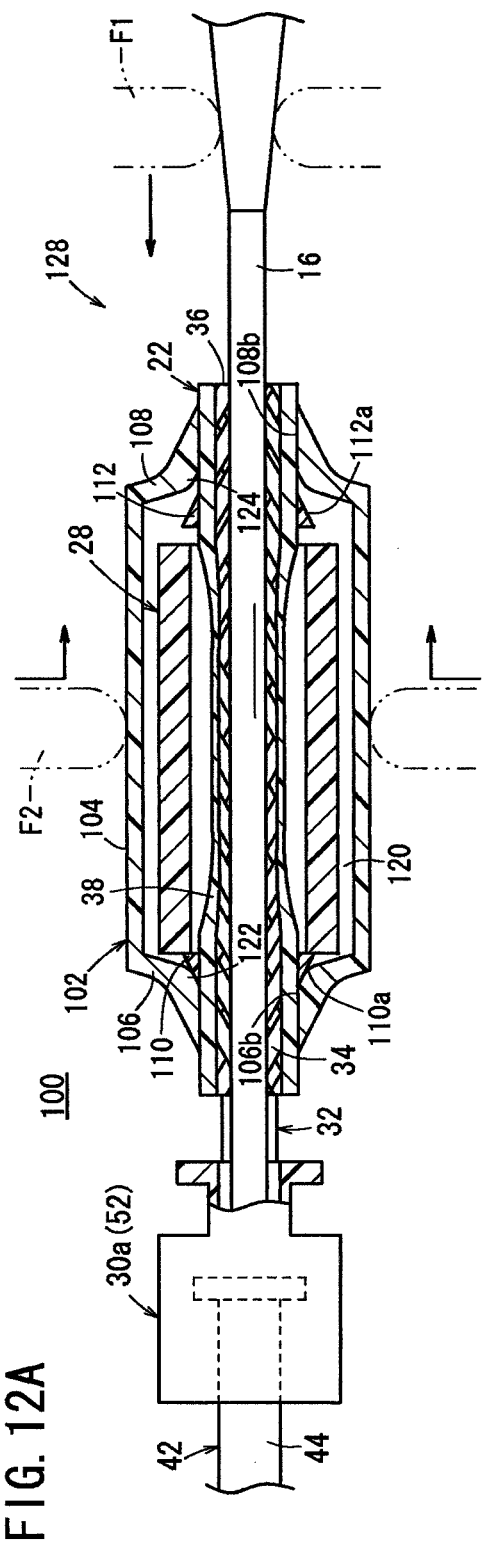
FIG. 12A shows a configuration where a tubular operating part is pushed inward and a force is exerted on an inner catheter in the proximal direction while holding the inner catheter, in using the fixing device according to the fourth embodiment.
Figure 12B:
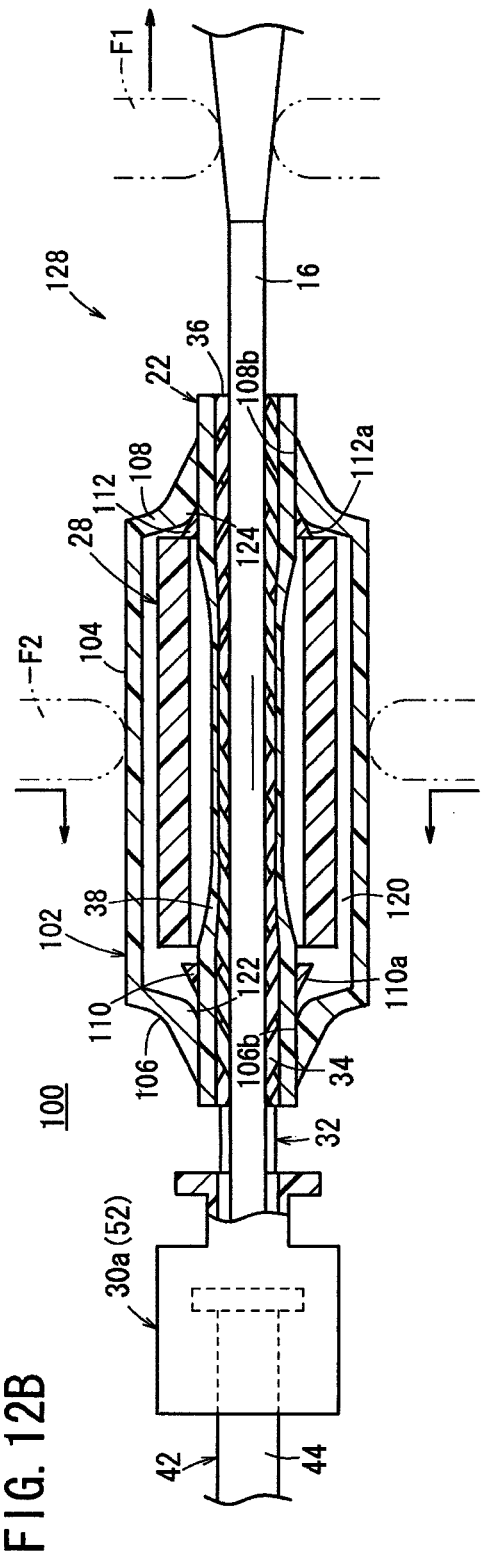
FIG. 12B shows a configuration where the tubular operating part is pushed inward and a force is exerted in the distal direction of the inner catheter while holding the inner catheter, in using the fixing device according to the fourth embodiment.

Now, the operation and effect of the fixing device 100 according to the fourth embodiment will be described below. In FIGS. 12A-12B, the fixing device 100 is mounted onto a shaft 16 of a catheter 14, whereby a catheter set 128 is configured. In addition, a catheter 14 with the fixing device 100 mounted thereto is inserted and passed in the lumen of an outer catheter 42, as an inner catheter, and a lock part 52 is fixed to a hub 44 of the outer catheter 42 through engagement, such as, for example, screw engagement. Incidentally, in the description to be made referring to FIGS. 12A to 13B, the catheter 14 will sometimes be referred to as "inner catheter 14."

Referring to FIG. 12A, in the case where the fixing device 100 is desired to be moved proximally relative to the catheter 14, the catheter 14 is held with fingers F1 on one side and, in this configuration, an arbitrary region of the trunk part 104 of the tubular operating part 102 is pinched with fingers F2 on the other side and is pressed radially inward, as shown by the directional arrows in FIG. 12A. This results in that the first engaging part 106 and the second engaging part 108 are reduced in diameter through elastic deformation together with the trunk part 104. When the first engaging part 106 and the second engaging part 108 are reduced in diameter, the first angular part 122 and the second angular part 124 are displaced away from each other in the axial direction.

When the tubular operating part 102 is pushed proximally while the first engaging part 106 and the second engaging part 108 are kept reduced in diameter, the first engaging part 106 and the second engaging part 108 are slid on the outer circumferential surface of the tubular member 22. Eventually, as shown in FIG. 12A, the first engaging part 106 comes into contact with the outer circumferential surface 110a of the first projection 110, and the first projection 110 makes contact with the distal end face of the movable tubular body 28. In this instance, the first angular part 122 of the first engaging part 106 is displaced in the direction away from the second projection 112 as compared with the case of the natural state. In addition, the first projection 110 is intermediately located between the first engaging part 106 and the movable tubular body 28. Therefore, the first angular part 122 does not come into abutment on the distal end face of the movable tubular body 28.

By these operations, the first projection 110 is pushed proximally by the first engaging part 106 of the tubular operating part 102, whereby the tubular member 22 is enlarged in diameter while contracting in the axial direction. The enlargement in diameter of the tubular member 22 releases the fixation of relative positions of the fixing device 100 and the catheter 14. Consequently, the fixing device 100 can be moved in the proximal direction along the catheter 14. When the inward pressure exerted on the tubular operating part 102 is released, the tubular operating part 102 is enlarged in diameter to the original state (natural state) by an elastically restoring force, resulting in that the first engaging part 106 and the first projection 110 are again spaced from each other, as shown in FIG. 11.

Referring to FIG. 12B, the case where the fixing device 100 is desired to be moved distally relative to the catheter 14, the catheter 14 is held with fingers F1 on one side, and, in this configuration, an arbitrary region of the trunk part 104 of the tubular operating part 102 is pinched with fingers F2 on the other side and pressed radially inward, as shown by the directional arrows in FIG. 12B. This results in that the first engaging part 106 and the second engaging part 108 are reduced in diameter through elastic deformation together with the trunk part 104. When the first engaging part 106 and the second engaging part 108 are reduced in diameter, the first angular part 122 and the second angular part 124 are displaced away from each other in the axial direction.

When the tubular operating part 102 is pushed distally while the first engaging part 106 and the second engaging part 108 are kept reduced in diameter, the first engaging part 106 and the second engaging part 108 are slid on the outer circumferential surface of the tubular member 22. Eventually, as shown in FIG. 12B, the second engaging part 108 comes into contact with the outer circumferential surface 112a of the second projection 112, and the second projection 112 makes contact with the proximal end face of the movable tubular body 28. In this instance, the second angular part 124 is displaced in the direction away from the first projection 110 as compared with the case of the natural state. In addition, the second projection 112 is intermediately located between the second engaging part 108 and the movable tubular body 28. Therefore, the second angular part 112 does not come into abutment on the proximal end face of the movable tubular body 28.

By these operations, the second projection 112 is pushed distally by the second engaging part 108 of the tubular operating part 102, whereby the tubular member 22 is enlarged in diameter while contracting in the axial direction. The enlargement in diameter of the tubular member 22 releases the fixation of relative positions of the fixing device 100 and the catheter 14. Consequently, the fixing device 100 can be moved in the distal direction along the catheter 14. When the inward pressure exerted on the tubular operating part 102 is released, the tubular operating part 102 is enlarged in diameter to the original state (i.e., natural state) by an elastically restoring force, resulting in that the second engaging part 108 and the second projection 112 are again spaced from each other, as shown in FIG. 11.

As understood from the above description, in the fixing device 100 according to this embodiment, the trunk part 104 of the tubular operating part 102 is pressed inward from both sides so that the first engaging part 106 and the second engaging part 108 are reduced in diameter, whereby the first projection 110 and the second projection 112 are put into the state of being able to be operated in the axial direction.

It should be understood by persons skilled in the art that in the fixing device 100, in the case where the above operation on the tubular operating part 102 is not performed, a function of fixing the relative positions of the catheter 14 and the fixing device 100 is exhibited, by the same operation as in the case of the fixing device 60 according to the third embodiment described above. Specifically, when forces are exerted on the inner catheter 14 and the outer catheter 42 in the direction for pulling the inner catheter 14 out of the outer catheter 42 in the configuration where the inner catheter 14 is held with fingers F1 on one side and the outer catheter 42 is held with fingers F2 on the other side, the engagement of the first projection 110 with the distal end of the movable tubular body 28 causes the tubular member 22 to be reduced in diameter while extending in the axial direction; therefore, relative movement of the outer catheter 42 and the inner catheter 14 is inhibited. When forces are applied to the inner catheter 14 and the outer catheter 42 in the direction for inserting the inner catheter 14 into the outer catheter 42 (i.e., in the direction for advancing the inner catheter 14 relative to the outer catheter 42) in the configuration where the inner catheter 14 is held with fingers F1 on one side and the outer catheter 42 is held with fingers F2 on the other side, due to the engagement of the second projection 112 with the proximal end of the movable tubular body 28, the tubular member 22 is reduced in diameter while extending in the axial direction. Consequently, relative movement of the outer catheter 42 and the inner catheter 14 is hampered.

The fixing device 60 according to the third embodiment is so configured that the position of the fixing device 60 relative to the catheter 14 can be easily changed by gripping the tubular operating part 62 and operating it in the axial direction. When an object comes into contact with the tubular operating part 62 in an unintentional manner, however, the fixation of the position of the fixing device 60 may be released due to the tubular operating part 62 being pushed in the axial direction by the object. On the other hand, the fixing device 100 according to this embodiment is so configured that, even when an object comes into contact with the tubular operating part 102 in an unintentional manner, the fixation of the relative positions of the catheter 14 and the fixing device 100 can be prevented from being released, as will be described below.

As shown in FIG. 13A, a case is assumed wherein an object M comes into contact with the tubular operating part 102, particularly the first engaging part 106, and a proximal pushing force is thereby exerted on the tubular operating part 102, as shown by the directional arrow in FIG. 13A. In this case, since the tubular operating part 102 is not in a diametrically reduced state, a proximal movement of the tubular operating part 102 results in that the first engaging part 106 does not make contact with the first projection 110. Instead, the first angular part 122 comes into abutment on the distal end face of the movable tubular body 28, and the proximal end face of the movable tubular body 28 comes into contact with the second projection 112. In this configuration, the tubular member 22 is not shortened in the axial direction and is not enlarged in diameter, so that the state in which relative movement of the catheter 14 and the fixing device 100 is inhibited is maintained.

Referring now to FIG. 13B, a case is assumed in which an object M comes into contact with the tubular operating part 102, particularly the second engaging part 108, and a distal pushing force is thereby exerted on the tubular operating part 102, as shown by the directional arrow in FIG. 13B. In this case, since the tubular operating part 102 is not in a diametrically reduced state, a distal movement of the tubular operating part 102 results in that the second engaging part 108 does not make contact with the second projection 112. Instead, the second angular part 124 comes into abutment on the proximal end face of the movable tubular body 28, and the distal end face of the movable tubular body 28 comes into contact with the first projection 110. In this configuration, the tubular member 22 is not shortened in the axial direction and is not enlarged in diameter, so that the state in which relative movement of the catheter 14 and the fixing device 100 is inhibited is maintained.

Incidentally, in the case where an object M comes into contact with the trunk part 104 of the tubular operating part 102 and an inward pressing force is thereby exerted on the trunk part 104, a configuration may be generated in which the first engaging part 106 and the second engaging part 108 are reduced in diameter to thereby enable the first projection 110 and the second projection 112 to be operated in the axial direction, like in FIGS. 12A and 12B. However, it is considered to be very difficult to move the fixing device 100 by changing the acting direction of the force of the object M to the axial direction. According to the fixing device 100, therefore, substantially most unintentional movements can be prevented from being generated.

As above-described, according to the fixing device 100 in this embodiment, an operation on the first projection 110 or the second projection 112 by the tubular operating part 102 is enabled only when the tubular operating part 102 is moved in the axial direction while being pressed inward. Therefore, even when an object M comes into contact with the tubular operating part 102 in an unintentional manner, the fixation of relative positions of the catheter 14 and the fixing device 100 can be effectively prevented from being released.

Besides, in this embodiment, the outer circumferential surface 110a of the first projection 110 and the inner circumferential surface 106b of the first projection 106 are formed to decrease in diameter along the distal direction of the fixing device 100, and the outer circumferential surface 112a of the second projection 112 and the inner circumferential surface 108b of the second engaging part 108 are formed to decrease in diameter along the proximal direction of the fixing device 100. This ensures that even when the tubular operating part 102 is moved in the axial direction in the natural state of the tubular operating part 102, the first engaging part 106 can be securely prevented from making contact with the first projection 110, and the second engaging part 108 can be securely prevented from making contact with the second projection 112.

Incidentally, in the fourth embodiment, those components which are provided in common in the third and fourth embodiments can naturally show operations and effects equal or similar to the operations and effects of such common components in the first embodiment.

Other Modification 1

Figure 14:
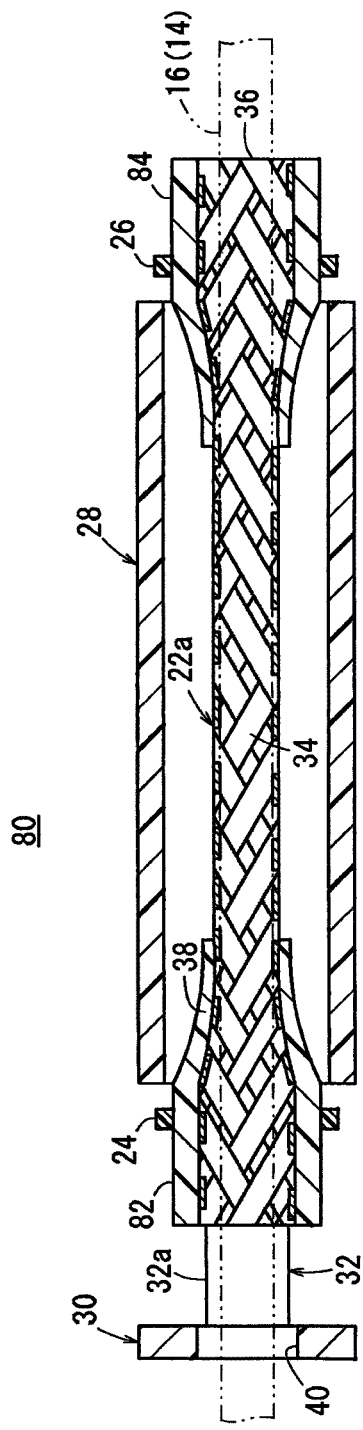
FIG. 14 is a longitudinal sectional view of a fixing device according to a first modification.

While the resin layer 38 is provided over the whole length of the braid 36 in the first to fourth embodiments described above, such a configuration as that of a tubular member 22a of a fixing device 80 shown in FIG. 14 may also be adopted. In this configuration, a resin layer is not provided on a longitudinally central part of the braid 36, but resin layers 82 and 84 are provided only in certain ranges including both end portions of the braid 36 and including the front and rear sides of the first projection 24 and the second projection 26. Such a configuration also ensures that the outer surfaces of both end portions of the braid 36 are prevented from being exposed, so that the operating feeling at the time when an end portion of the tubular member 22a is touched and operated by the user can be enhanced.

Other Modification 2

Figure 15:
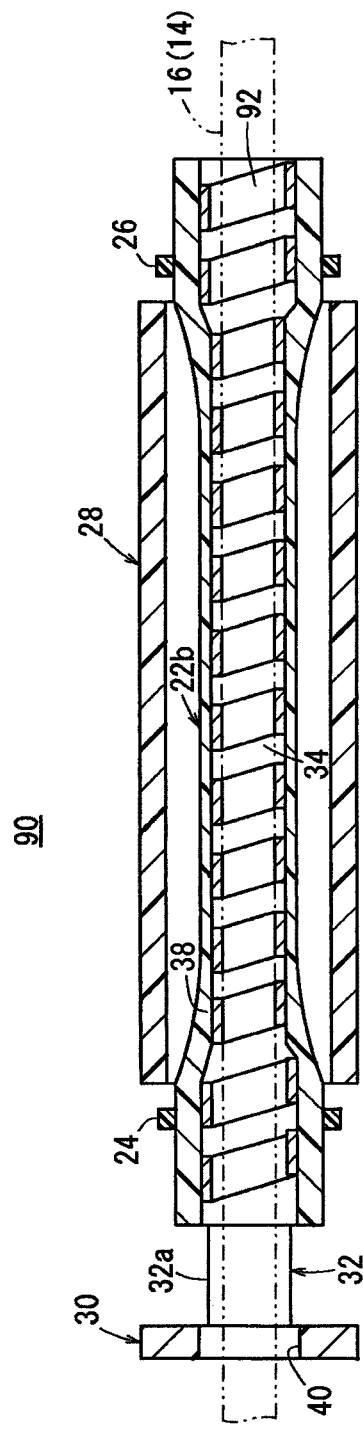
FIG. 15 is a longitudinal sectional view of a fixing device according to a second modification.

While the tubular member 22 composed of the braid 36 is applied in the first to fourth embodiments described above, such a configuration as that of a fixing device 90 shown in FIG. 15 may also be adopted, in which a tubular member 22b is composed of a coil member 92. In this case, as shown in FIG. 15, the coil member 92 is preferably one that is produced by spirally winding a material which is flat plate-shaped in section, although it may be one that is produced by spirally winding a linear material which is circular in section, in order that the coil member 92 has a small number of turns.

Where the coil member 92 is formed from a material which is flat plate-shaped in section, the area of contact with the shaft 16 is greater, and a sufficient frictional force can be more easily obtained at the time of reduction in diameter, as compared with the case where the coil member 92 is formed from a linear material which is circular in section. In addition, due to high rigidity, better force transmission can be realized when a force is exerted from one end portion toward the other end portion in the longitudinal direction. As a result, the coil member 92 is enlarged in diameter sufficiently, and the frictional force acting on the shaft 16 is released assuredly, whereby relative movements of the fixing device 90 and the catheter 14 can be permitted.

While the present invention has been described above by showing preferred embodiments, the invention is not restricted to the above-described embodiments and, naturally, various alterations are possible within the scope of the invention.

What is claimed is:

1. A fixing device configured for mounting to a shaft of a catheter and arbitrarily changing the mounting position and fixing thereof, the fixing device comprising:
   a tubular member having a hollow part permitting the shaft to be inserted and passed therein, the tubular member being configured such that the hollow part is enlarged by contraction of the tubular member in an axial direction and reduced by extension of the tubular member in the axial direction;
   a first projection and a second projection which are provided on an outer circumferential portion of the tubular member at positions spaced from each other in the axial direction of the tubular member;
   a movable tubular body which is disposed around the tubular member between the first projection and the second projection, the tubular body being configured for movement in the axial direction relative to the tubular member within a range restricted by the first projection and the second projection; and
  a distal part coupled with the movable tubular body by a support part, the distal part being disposed distally of the tubular member, the distal part being configured to contact a proximal portion of a tubular device for medical use in a configuration wherein the fixing device is mounted to the catheter, and the catheter is inserted and passed in a lumen of the tubular device for medical use.

2. The fixing device according to claim 1, wherein the distal part comprises a lock part, the lock part being configured to releasably engage with the tubular device for medical use.

3. The fixing device according to claim 1, further comprising:
  a tubular operating part which accommodates the movable tubular body, the first projection, and the second projection, the tubular operating part being movable in the axial direction relative to the tubular member and the movable tubular body,
  wherein the tubular operating part has a first engaging part disposed distally relative to the movable tubular body and a second engaging part disposed proximally relative to the movable tubular body,
  the first projection has a relative movement range restricted between the first engaging part and a distal end of the movable tubular body, and
  the second projection has a relative movement range restricted between the second engaging part and a proximal end of the movable tubular body.

4. The fixing device according to claim 1, further comprising:
  a tubular operating part which accommodates the movable tubular body, the first projection, and the second projection, the tubular operating part being movable in the axial direction relative to the tubular member and the movable tubular body,
  wherein the tubular operating part has a trunk part surrounding the movable tubular body with a gap therebetween in its natural state, a first engaging part provided on a distal side of the trunk part, and a second engaging part provided on a proximal side of the trunk part, the tubular operating part being configured such that
  the first engaging part and the second engaging part are elastically decreased in diameter together with the trunk part when an inward pressing force is exerted on the trunk part,
  an inner circumferential portion of the first engaging part makes contact with an outer circumferential portion of the tubular member distally relative to the first projection, and an inner circumferential portion of the second engaging part makes contact with an outer circumferential portion of the tubular member proximally relative to the second projection, and
  the first engaging part is configured to make contact with a distal end of the movable tubular body in the state of being spaced from the first projection when the tubular operating part is in a natural state, and is configured to make contact with the first projection and operating the first projection in the axial direction when the tubular operating part is in a diametrically decreased state, and
  the second engaging part is configured to make contact with a proximal end of the movable tubular body in the state of being spaced from the second projection when the tubular operating part is in a natural state, and is configured to make contact with the second projection and operating the second projection in the axial direction when the tubular operating part is in the diametrically decreased state.

5. The fixing device according to claim 4,
  wherein the first projection has an outer circumferential surface decreasing in outside diameter in a distally from the second projection in the axial direction,
  the first engaging part has an inner circumferential surface decreasing in inside diameter distally from the second engaging part in the axial direction,
  the second projection has an outer circumferential surface decreasing in outside diameter proximally from the first projection in the axial direction, and
  the second engaging part has an inner circumferential surface decreasing in inside diameter proximally from the first engaging part in the axial direction.

6. The fixing device according to claim 1,
  wherein the tubular member is a braid obtained by braiding fine strands.

7. The fixing device according to claim 1,
  wherein the support part comprises a pair of arms extending in the distal direction from the movable tubular body, and
  the first projection projects outward between the pair of arms.

8. A catheter set comprising:
  a catheter having a shaft;
  a fixing device configured for mounting to the shaft of the catheter and arbitrarily changing the mounting position and fixing thereof, the fixing device comprising:
    a tubular member having a hollow part permitting the shaft to be inserted and passed therein, the tubular member being configured such that the hollow part is enlarged by contraction of the tubular member in an axial direction and reduced by extension of the tubular member in the axial direction;
    a first projection and a second projection which are provided on an outer circumferential portion of the tubular member at positions spaced from each other in the axial direction of the tubular member;
    a movable tubular body which is disposed around the tubular member between the first projection and the second projection, the tubular body being configured for movement in the axial direction relative to the tubular member within a range restricted by the first projection and the second projection; and
    a distal part coupled with the movable tubular body by a support part, the distal part being disposed distally of the tubular member, the distal part being configured to contact a proximal portion of a tubular device for medical use in a configuration wherein the fixing device is mounted to the catheter, and the catheter is inserted and passed in a lumen of the tubular device for medical use.

9. The catheter set according to claim 8, wherein the distal part comprises a lock part, the lock part being configured to releasably engage with the tubular device for medical use.

10. The catheter set according to claim 8, further comprising:
  a tubular operating part which accommodates the movable tubular body, the first projection, and the second projection, the tubular operating part being movable in the axial direction relative to the tubular member and the movable tubular body,
  wherein the tubular operating part has a first engaging part disposed distally relative to the movable tubular body and a second engaging part disposed proximally relative to the movable tubular body, the first projection has a relative movement range restricted between the first engaging part and a distal end of the movable tubular body, and the second projection has a relative movement range restricted between the second engaging part and a proximal end of the movable tubular body.

11. The catheter set according to claim 8, further comprising:

a tubular operating part which accommodates the movable tubular body, the first projection, and the second projection, the tubular operating part being movable in the axial direction relative to the tubular member and the movable tubular body, wherein the tubular operating part has a trunk part surrounding the movable tubular body with a gap therebetween in its natural state, a first engaging part provided on a distal side of the trunk part, and a second engaging part provided on a proximal side of the trunk part, the tubular operating part being configured such that the first engaging part and the second engaging part are elastically decreased in diameter together with the trunk part when an inward pressing force is exerted on the trunk part, an inner circumferential portion of the first engaging part makes contact with an outer circumferential portion of the tubular member distally relative to the first projection, and an inner circumferential portion of the second engaging part makes contact with an outer circumferential portion of the tubular member proximally relative to the second projection, and the first engaging part is configured to make contact with a distal end of the movable tubular body in the state of being spaced from the first projection when the tubular operating part is in a natural state, and is configured to make contact with the first projection and operating the first projection in the axial direction when the tubular operating part is in a diametrically decreased state, and the second engaging part is configured to make contact with a proximal end of the movable tubular body in the state of being spaced from the second projection when the tubular operating part is in a natural state, and is configured to make contact with the second projection and operating the second projection in the axial direction when the tubular operating part is in the diametrically decreased state.

12. The catheter set according to claim 11, wherein the first projection has an outer circumferential surface decreasing in outside diameter in a distally from the second projection in the axial direction, the first engaging part has an inner circumferential surface decreasing in inside diameter distally from the second engaging part in the axial direction, the second projection has an outer circumferential surface decreasing in outside diameter proximally from the first projection in the axial direction, and the second engaging part has an inner circumferential surface decreasing in inside diameter proximally from the first engaging part in the axial direction.

13. The catheter set according to claim 8, wherein the tubular member is a braid obtained by braiding fine strands.

14. The catheter set according to claim 8, wherein the support part comprises a pair of arms extending in the distal direction from the movable tubular body, and the first projection projects outward between the pair of arms.

15. A fixing device configured for mounting to a shaft of a catheter and arbitrarily changing the mounting position and fixing thereof, the fixing device comprising:

a tubular member having a hollow part permitting the shaft to be inserted and passed therein, the tubular member being configured such that the hollow part is enlarged by contraction of the tubular member in an axial direction and reduced by extension of the tubular member in the axial direction;

a first projection and a second projection which are provided on an outer circumferential portion of the tubular member at positions spaced from each other in the axial direction of the tubular member;

a movable tubular body which is disposed around the tubular member between the first projection and the second projection, the tubular body being movable relative to the tubular member between the first projection and the second projection in the axial direction; and an assembly coupled with and extending distally from the movable tubular body, the assembly having a distal portion spaced from a distal end of the movable tubular body and configured to contact or receive a proximal portion of a tubular device for medical use in a configuration wherein the fixing device is mounted to the catheter, and the catheter is inserted and passed in a lumen of the tubular device for medical use.

16. The fixing device according to claim 15, wherein the distal portion comprises a lock part, the lock part being configured to releasably engage with the tubular device for medical use.

17. The fixing device according to claim 15, further comprising:

a tubular operating part which accommodates the movable tubular body, the first projection, and the second projection, the tubular operating part being movable in the axial direction relative to the tubular member and the movable tubular body, the tubular operating part having a first engaging part disposed distally relative to the movable tubular body and a second engaging part disposed proximally relative to the movable tubular body, the first projection having a relative movement range restricted between the first engaging part and a distal end of the movable tubular body, and the second projection having a relative movement range restricted between the second engaging part and a proximal end of the movable tubular body.

18. The fixing device according to claim 15, further comprising:

a tubular operating part which accommodates the movable tubular body, the first projection, and the second projection, the tubular operating part being movable in the axial direction relative to the tubular member and the movable tubular body, the tubular operating part having a trunk part surrounding the movable tubular body with a gap therebetween in its natural state, a first engaging part provided on a distal side of the trunk part, and a second engaging part provided on a proximal side of the trunk part, the tubular operating part being configured such that the first engaging part and the second engaging part are elastically decreased in diameter together with the trunk part when an inward pressing force is exerted on the trunk part, an inner circumferential portion of the first engaging part makes contact with an outer circumferential portion of the tubular member distally relative to the first projection, and an inner circumferential portion of the second engaging part makes contact with an outer circumferential portion of the tubular member proximally relative to the second projection, and the first engaging part being configured to make contact with a distal end of the movable tubular body in the state of being spaced from the first projection when the tubular operating part is in a natural state, and is configured to make contact with the first projection and operating the first projection in the axial direction when the tubular operating part is in a diametrically decreased state, and the second engaging part is configured to make contact with a proximal end of the movable tubular body in the state of being spaced from the second projection when the tubular operating part is in a natural state, and is configured to make contact with the second projection and operating the second projection in the axial direction when the tubular operating part is in the diametrically decreased state.

19. The fixing device according to claim 18, wherein the first projection has an outer circumferential surface decreasing in outside diameter in a distally from the second projection in the axial direction, the first engaging part having an inner circumferential surface decreasing in inside diameter distally from the second engaging part in the axial direction, the second projection having an outer circumferential surface decreasing in outside diameter proximally from the first projection in the axial direction, and the second engaging part having an inner circumferential surface decreasing in inside diameter proximally from the first engaging part in the axial direction.

20. The fixing device according to claim 15, wherein the assembly includes a pair of support arms extending distally from the movable tubular body to the distal portion of the assembly, the first projection projects outward between the pair of arms.

* * * * *